(12) United States Patent
Tanaka et al.

(10) Patent No.: US 7,341,561 B2
(45) Date of Patent: Mar. 11, 2008

(54) WRIST-WORN HIGH-ACCURACY PULSATION MEASURING APPARATUS

(75) Inventors: Shinichi Tanaka, Tsurugashima (JP); Yoshiyuki Murata, Ome (JP)

(73) Assignee: Casio Computer Co., Ltd., Tokyo (JP)

( * ) Notice: Subject to any disclaimer, the term of this patent is extended or adjusted under 35 U.S.C. 154(b) by 702 days.

(21) Appl. No.: 10/853,729

(22) Filed: May 24, 2004

(65) Prior Publication Data
US 2004/0243009 A1 Dec. 2, 2004

(30) Foreign Application Priority Data
May 30, 2003 (JP) .............................. 2003-154563
Jun. 16, 2003 (JP) .............................. 2003-170598

(51) Int. Cl.
*A61B 5/02* (2006.01)
(52) U.S. Cl. ..................... 600/503; 600/344; 600/490; 600/494; 600/499
(58) Field of Classification Search ............... 600/503, 600/485, 513, 344, 490, 494, 496, 453, 499, 600/481, 500, 585, 587, 549, 459; 340/573.1; 128/878; 310/322; 403/322.1
See application file for complete search history.

(56) References Cited

U.S. PATENT DOCUMENTS

| | | | | |
|---|---|---|---|---|
| 2,854,968 A | * | 10/1958 | Wright | 600/503 |
| 3,535,067 A | * | 10/1970 | Lesher et al. | 600/485 |
| 3,903,873 A | * | 9/1975 | Royal et al. | 600/502 |
| 4,086,916 A | * | 5/1978 | Freeman et al. | 600/453 |
| 4,096,854 A | * | 6/1978 | Perica et al. | 600/503 |
| 4,185,621 A | * | 1/1980 | Morrow | 600/485 |
| 4,224,948 A | * | 9/1980 | Cramer et al. | 600/503 |
| 4,331,154 A | * | 5/1982 | Broadwater et al. | 600/490 |
| 4,407,295 A | * | 10/1983 | Steuer et al. | 600/483 |
| 4,489,731 A | * | 12/1984 | Baumberg | 600/503 |
| 4,761,582 A | * | 8/1988 | McKee | 310/322 |
| 4,784,152 A | * | 11/1988 | Shinoda et al. | 600/503 |
| 4,802,488 A | * | 2/1989 | Eckerle | 600/485 |
| 4,867,170 A | * | 9/1989 | Takahashi | 600/490 |
| 4,896,676 A | * | 1/1990 | Sasaki | 600/494 |
| 4,901,733 A | * | 2/1990 | Kaida et al. | 600/500 |
| 4,909,260 A | * | 3/1990 | Salem et al. | 600/534 |
| 4,987,900 A | * | 1/1991 | Eckerle et al. | 600/485 |
| 5,131,400 A | * | 7/1992 | Harada et al. | 600/500 |
| 5,152,302 A | * | 10/1992 | Fareed | 128/878 |

(Continued)

*Primary Examiner*—Charles A. Marmor, II
*Assistant Examiner*—Anita Saidi
(74) *Attorney, Agent, or Firm*—Frishauf, Holtz, Goodman & Chick, P.C.

(57) ABSTRACT

A wrist-worn apparatus capable of sensing pulsation of blood in the blood tubes of a user's wrist with high accuracy. The apparatus comprises a body of the apparatus, a band to be used to wear the body of the apparatus on the user's wrist, and a fluid-containing pulsation-sensing fluid chamber provided on the user's wrist side of the case. A part of an outer wall that defines the fluid chamber comprises an elastically deformable member that is elastically deformed depending on pulsation of blood transmitted from the band to thereby change the fluid pressure within the fluid chamber. A deformation preventing member is bonded by vulcanization to a part of a side of the deformable member that will come into contact with the user's wrist for preventing the part of the deformable member from being elastically deformed.

10 Claims, 22 Drawing Sheets

U.S. PATENT DOCUMENTS

| | | | |
|---|---|---|---|
| 5,179,956 A * | 1/1993 | Harada et al. | 600/485 |
| 5,238,000 A * | 8/1993 | Niwa | 600/502 |
| 5,240,007 A * | 8/1993 | Pytel et al. | 600/485 |
| 5,243,992 A * | 9/1993 | Eckerle et al. | 600/503 |
| 5,261,414 A * | 11/1993 | Aung et al. | 600/496 |
| 5,269,312 A * | 12/1993 | Kawamura et al. | 600/503 |
| 5,351,694 A * | 10/1994 | Davis et al. | 600/485 |
| 5,450,852 A * | 9/1995 | Archibald et al. | 600/485 |
| 5,467,771 A * | 11/1995 | Narimatsu et al. | 600/485 |
| 5,497,779 A * | 3/1996 | Takaya et al. | 600/485 |
| 5,509,423 A * | 4/1996 | Bryars | 600/503 |
| 5,649,542 A * | 7/1997 | Archibald et al. | 600/485 |
| 5,722,414 A * | 3/1998 | Archibald et al. | 600/485 |
| 5,735,800 A * | 4/1998 | Yasukawa et al. | 600/503 |
| 5,759,156 A * | 6/1998 | Hayakawa et al. | 600/483 |
| 5,787,054 A * | 7/1998 | Yasukawa et al. | 368/204 |
| 5,795,300 A * | 8/1998 | Bryars | 600/500 |
| 5,807,267 A * | 9/1998 | Bryars et al. | 600/500 |
| 5,810,736 A * | 9/1998 | Pail | 600/500 |
| 5,894,454 A * | 4/1999 | Kondo | 368/11 |
| 5,908,396 A * | 6/1999 | Hayakawa et al. | 600/587 |
| 5,941,828 A * | 8/1999 | Archibald et al. | 600/494 |
| 5,984,874 A * | 11/1999 | Cerwin | 600/549 |
| 6,080,111 A * | 6/2000 | Pao-Lang | 600/503 |
| 6,155,983 A * | 12/2000 | Kosuda et al. | 600/500 |
| 6,314,058 B1 * | 11/2001 | Lee | 368/10 |
| 6,334,850 B1 * | 1/2002 | Amano et al. | 600/500 |
| 6,402,417 B1 * | 6/2002 | Okamoto | 403/322.1 |
| 6,440,081 B1 * | 8/2002 | Yang | 600/503 |
| 6,443,906 B1 * | 9/2002 | Ting et al. | 600/490 |
| 6,491,647 B1 * | 12/2002 | Bridger et al. | 600/585 |
| 6,529,754 B2 * | 3/2003 | Kondo | 600/344 |
| 6,589,185 B1 * | 7/2003 | Archibald et al. | 600/494 |
| 6,605,045 B2 * | 8/2003 | Ohsaki et al. | 600/503 |
| 6,626,837 B2 * | 9/2003 | Muramatsu et al. | 600/459 |
| 6,811,535 B2 * | 11/2004 | Palti et al. | 600/499 |
| 6,887,205 B2 * | 5/2005 | Nakamura et al. | 600/459 |
| 6,918,879 B2 * | 7/2005 | Ting et al. | 600/485 |
| D508,038 S * | 8/2005 | Bonadei | D14/138 |
| 6,982,930 B1 * | 1/2006 | Hung | 368/10 |
| D516,724 S * | 3/2006 | Inagaki et al. | D24/165 |
| 7,018,338 B2 * | 3/2006 | Vetter et al. | 600/503 |
| 7,083,573 B2 * | 8/2006 | Yamakoshi et al. | 600/485 |
| 7,144,375 B2 * | 12/2006 | Kosuda | 600/503 |
| D540,695 S * | 4/2007 | Leung | D10/31 |
| 7,214,193 B2 * | 5/2007 | Freund et al. | 600/490 |
| 7,215,601 B2 * | 5/2007 | Plancon et al. | 368/10 |
| 2001/0020134 A1 * | 9/2001 | Nissila et al. | 600/503 |
| 2001/0056240 A1 * | 12/2001 | Palti et al. | 600/481 |
| 2001/0056243 A1 * | 12/2001 | Ohsaki et al. | 600/503 |
| 2002/0013534 A1 * | 1/2002 | Muramatsu et al. | 600/503 |
| 2002/0077558 A1 * | 6/2002 | Itonaga et al. | 600/490 |
| 2002/0095092 A1 * | 7/2002 | Kondo et al. | 600/503 |
| 2002/0109600 A1 * | 8/2002 | Mault et al. | 340/573.1 |
| 2002/0123691 A1 * | 9/2002 | Yang | 600/503 |
| 2002/0147404 A1 * | 10/2002 | Kato et al. | 600/503 |
| 2002/0151775 A1 * | 10/2002 | Kondo | 600/344 |
| 2002/0188210 A1 * | 12/2002 | Aizawa | 600/503 |
| 2003/0065269 A1 * | 4/2003 | Vetter et al. | 600/503 |
| 2005/0010119 A1 * | 1/2005 | Palti et al. | 600/499 |
| 2005/0049514 A1 * | 3/2005 | Iwamiya et al. | 600/503 |
| 2005/0234351 A1 * | 10/2005 | Nishii et al. | 600/503 |
| 2005/0251059 A1 * | 11/2005 | Kim | 600/513 |
| 2006/0047207 A1 * | 3/2006 | Itonaga et al | 600/500 |
| 2006/0079792 A1 * | 4/2006 | Finburgh et al. | 600/485 |
| 2006/0122521 A1 * | 6/2006 | Chen | 600/503 |

* cited by examiner

WRIST-WORN HIGH-ACCURACY PULSATION MEASURING APPARATUS

TECHNICAL FIELD

The present invention relates to wrist-worn apparatus, and more particularly to such apparatus having a living-body information sensing function and/or a timepiece function.

BACKGROUND ART

In the past, wristwatches having a timepiece function and a function to measure living-body data such as pulsation/blood pressure are known. Such a wristwatch has, for example, an air chamber and a cuff that fluid communicates with the air chamber within a case thereof with a pressure sensor extending into the air chamber. In this wristwatch, the air within the cuff is intermittently pressurized in accordance with pulsation of blood in the blood tubes within a user's wrist. Resulting changes in the air pressure are transmitted into the air chamber. Changes in the air pressure within the air chamber are sensed by the pressure sensor, thereby displaying the changes as blood pressure or pulsation.

The whole cuff is molded from an elastically deformable material such that after the cuff is deformed elastically by the pressure, it will be restored to its original state due to elasticity.

When the whole cuff is molded from the elastic material, however, only that part of the cuff that comes directly into contact with the user's wrist will absorb the push force given by the pulsation. Thus, the cuff would be elastically deformed locally. Therefore, a uniform change cannot be produced in the air pressure within the fluid chamber and hence high accuracy of pulsation measurement is difficult to obtain.

It is therefore an object of the present invention to provide a wrist-worn apparatus capable of sensing pulsation of blood in the blood tubes of the user's wrist with high accuracy.

SUMMARY OF THE INVENTION

In order to achieve the above object, the present invention provides a wrist-worn apparatus comprising: the body of the apparatus; and a band attached to the body of the apparatus to be used for wearing the body of the apparatus on a user's wrist; the body of the apparatus comprising a pulsation sensing unit that in turn comprises a pulsation sensing fluid chamber containing a fluid and having a bottom that will come into contact with the user's wrist when the body of the apparatus is worn on the user's wrist, the fluid chamber having an outer wall that defines the fluid chamber and that comprises the bottom, the outer wall comprising an elastically deformable member elastically deformed depending on pulsation of blood in the blood tubes of the user's wrist transmitted through the band from the user's wrist when the body of the apparatus is worn on the user's wrist to thereby change the fluid pressure within the fluid chamber; and a deformation preventing member provided on the bottom of the fluid chamber for preventing its elastic deformation.

The present invention also provides a wrist-worn apparatus comprising: a body of the apparatus; and a band attached to the body of the apparatus to be used for wearing the body of the apparatus on the user's wrist; and the body of the apparatus comprising a pulsation sensing fluid chamber containing a fluid and that will come into contact with the user's wrist when the body of the apparatus is worn on the user's wrist, the fluid chamber having an outer wall that defines the fluid chamber, the outer wall and the band being molded integral with each other and made of a soft material.

The present invention further provides a wrist-worn apparatus comprising: a body of the apparatus; and a band attached to the body of the apparatus to be used for wearing the body of the apparatus on the user's wrist; and the body of the apparatus comprising a pulsation measuring unit that in turn comprises a pulsation sensing fluid chamber that contains a fluid and that will come into contact with the user's wrist when the body of the apparatus is worn on the user's wrist, the pulsation sensing unit comprising a pulsation sensor provided within the pulsation sensing fluid chamber for sensing changes in the fluid pressure within the fluid chamber as pulsation of blood in the blood tubes of the user's wrist, the sensor being positioned at a position deviating the center of the fluid chamber.

The present invention also provides a wrist-worn apparatus comprising: a body of the apparatus; and a band attached to the body of the apparatus to be used for wearing the body of the apparatus on a user's wrist; the body of the apparatus comprising a pulsation sensing unit that in turn comprises a pulsation sensing fluid chamber containing a fluid and having a bottom that will come into contact with the user's wrist when the body of the apparatus is worn on the user's wrist, the fluid chamber having an outer wall that defines the fluid chamber and that comprises the bottom, the outer wall comprising an elastically deformable member elastically deformed depending on pulsation of blood in the blood tubes of the user's wrist transmitted through the band from the user's wrist when the body of the apparatus is worn on the user's wrist to thereby change the fluid pressure within the fluid chamber; and a deformation preventing member bonded by vulcanization to the bottom of the fluid chamber for preventing its elastic deformation.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which.

DETAILED DESCRIPTION

Figure 1:
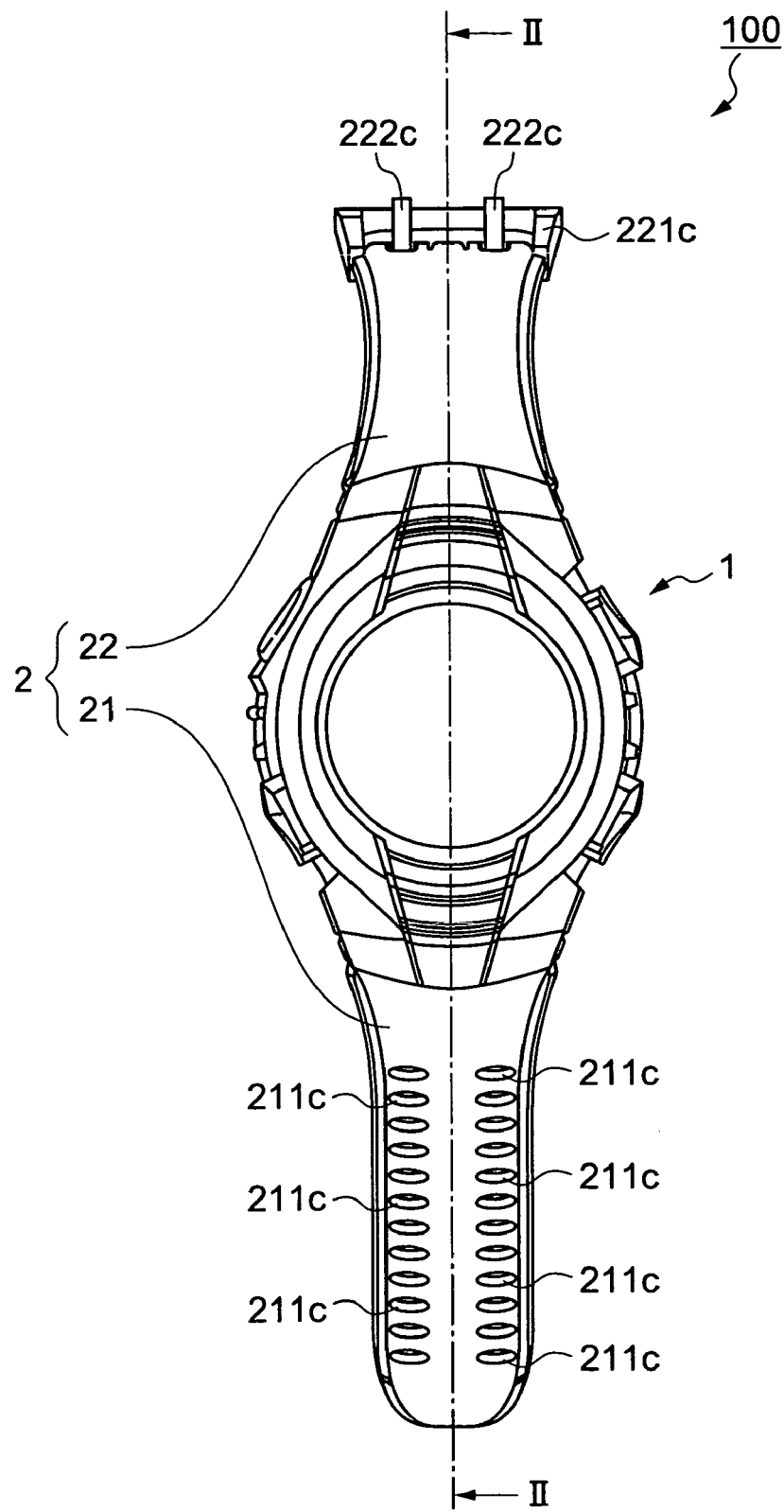
FIG. 1 is a plan view of a wristwatch according to the present invention.

Preferred embodiments of the wrist-worn apparatus having a pulsation-measuring function according to the present invention will be described as an example in more detail with respect to the accompanying drawings. The same reference numerals are used to denote like parts in the drawings.

Embodiment 1

First, referring to FIGS. 1-5, an embodiment 1 of the wristwatch according to the present invention will be described. As shown in FIG. 1, the wristwatch 100 comprises the body of the wristwatch, and a band 2 by which the body of the wristwatch is worn on a user's wrist W. The body of the wristwatch comprises including a case 1, the components of the wristwatch housed within the case 1, and a pulsation measuring unit 3 that comprises an air fluid chamber 5 provided to the case 1 so that when the wristwatch is worn on the user's wrist W, the bottom of the fluid chamber 5 comes into contact with the user's wrist. The air fluid chamber 5 contains therein a piezoelectric element 34 that measures pulsation of blood in the blood tubes of the user's wrist W by sensing changes in the air pressure within fluid chamber 5.

Figure 2:
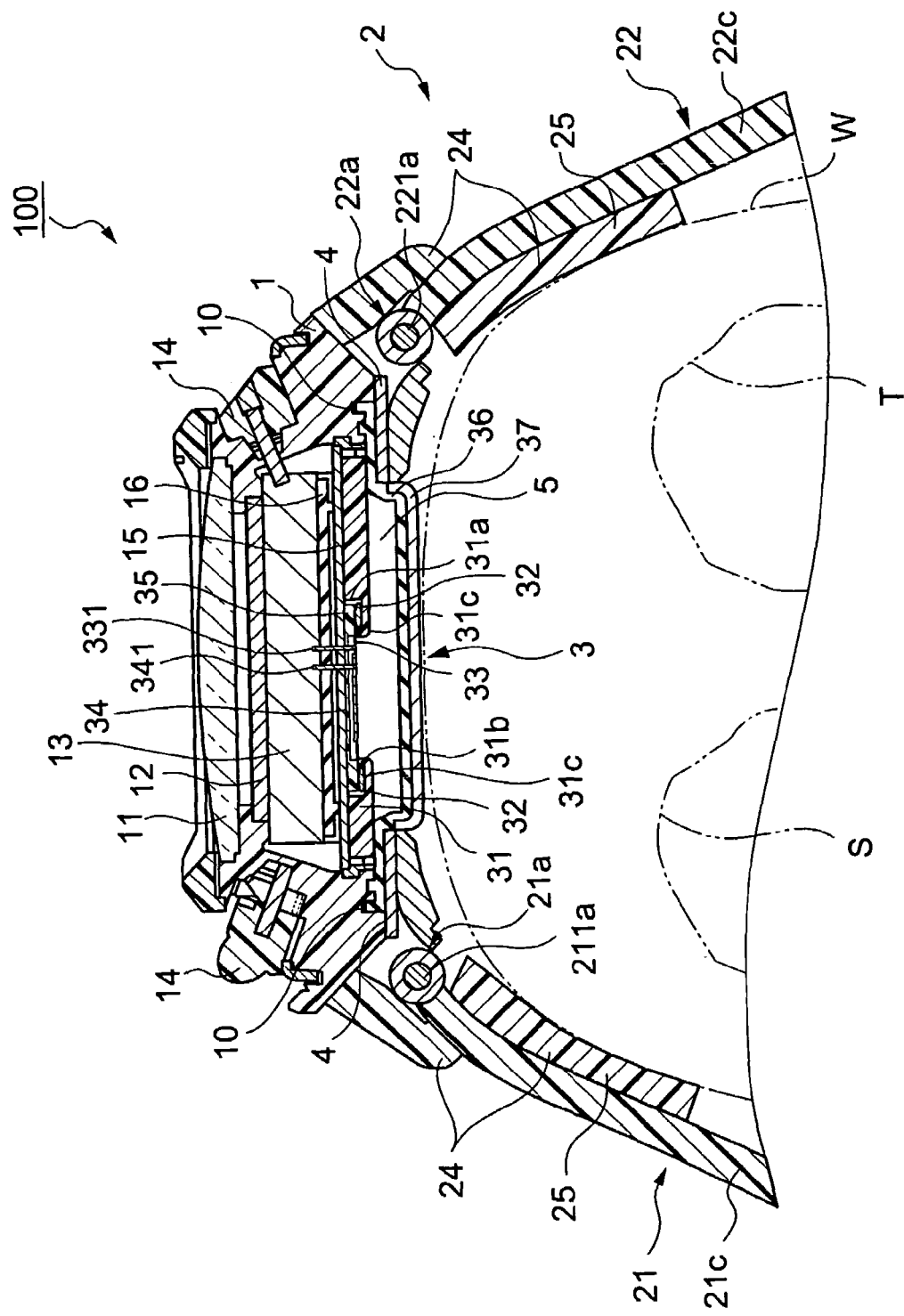
FIG. 2 is a cross-sectional view of an embodiment 1 of the wristwatch taken along a line II-II in FIG. 1.

As shown in FIG. 2, the case 1 is in substantially the form of a hollow cylinder with a crystal 11 on top thereof. A display 12 that displays time/pulsation is provided within the case 1 below the crystal 11. A timepiece function unit 13 is provided to a lower surface of the display 12 and connected electrically to the display 12. Operation keys 14 are provided on the outer surface of the case 1 so as to extend through the case 1 to the timepiece function unit 13 for allowing the user to manipulate the wristwatch 100. By depressing any one of the keys 14, a corresponding circuit is completed within the timepiece function unit 13 to thereby perform a corresponding operation. A partition plate 15 molded, for example, from a stainless steel (SUS) partitions the space within the case 1. A support member 16 that supports the timepiece function unit 13 is provided above the partition plate 15 below which the pulsation measuring unit 3 is provided.

As shown in FIGS. 1 and 2, the band 2 comprises a first band portion 21 and a second band portion 22 which are connected at one end to opposite sides of the case 1.

More specifically, the first band portion 21 has a connecting end 21a that connects the first band portion 21 to the case 1, and a main band portion 21c continuous to the end 21a and adapted to be wound around the user's wrist W.

The connecting end 21a is molded, for example, from leather or urethane with a pivot 211a that is received in a hole in a corresponding one of the opposite sides of the case 1, thereby connecting the first band portion 21 to the case 1 pivotally.

The main band portion 21c is molded, for example, from leather of urethane and has a plurality of holes 211c (FIG. 1) arranged therein along its length.

The second band portion 22 has a connecting end 22a that connects the second band portion 22 to the case 1, and a main band portion 22c continuous to the end 22a and adapted to be wound around the user's wrist W to thereby be connected to the main band portion 21c.

The connecting end 22a is molded, for example, from leather or urethane with a pivot 221a that is received in a hole in the other of the opposite sides of the case 1, thereby connecting the second band portion 22 to the case 1 pivotally.

The main band portion 22c is also molded, for example, from leather or urethane and has a buckle 221c with engaging pawls 222c at an opposite end thereof from the connecting end 22a.

As shown in FIG. 2, the wristwatch 100 also includes two substantially cylindrical covers 24 that extend so as to surround the connecting ends 21a and 22a and base ends 21c and 22c of the first and second band portions 21 and 22, respectively. Each cover 24 has a guide 25 provided on a back of each of the main band portions 21c and 22c so as to extend along that main band portion. Each guide 25 serves to restrict the bending of each of the main band portions 21c and 22c toward the user's wrist W when the wristwatch 100 is worn on the user's wrist.

Figure 3:
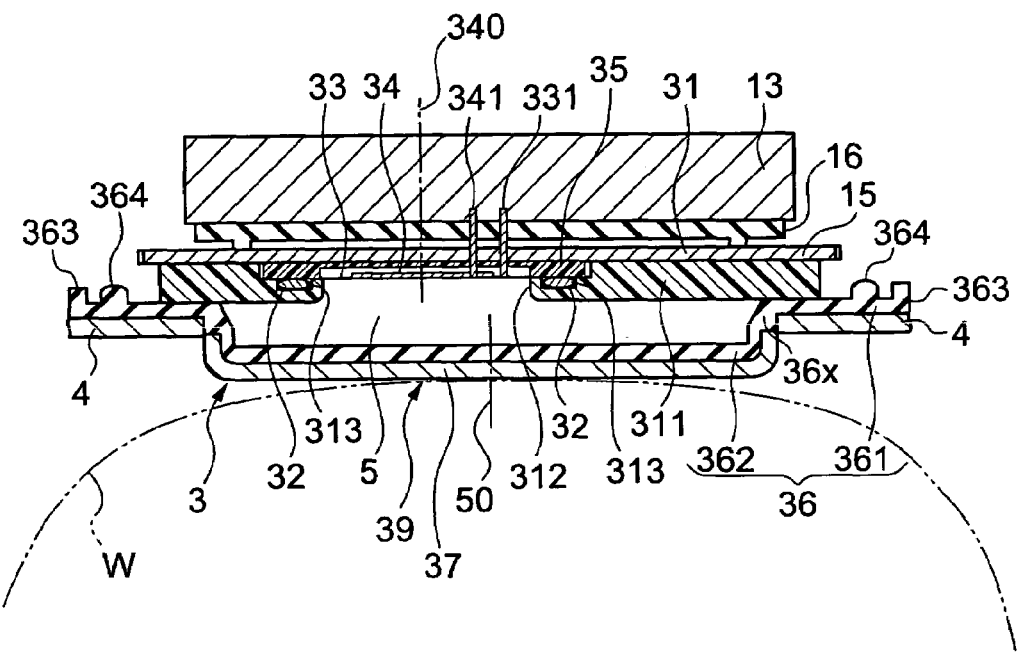
FIG. 3 is an enlarged cross-sectional view of a pulsation measuring unit of the wristwatch in the embodiment 1.
Figure 4:
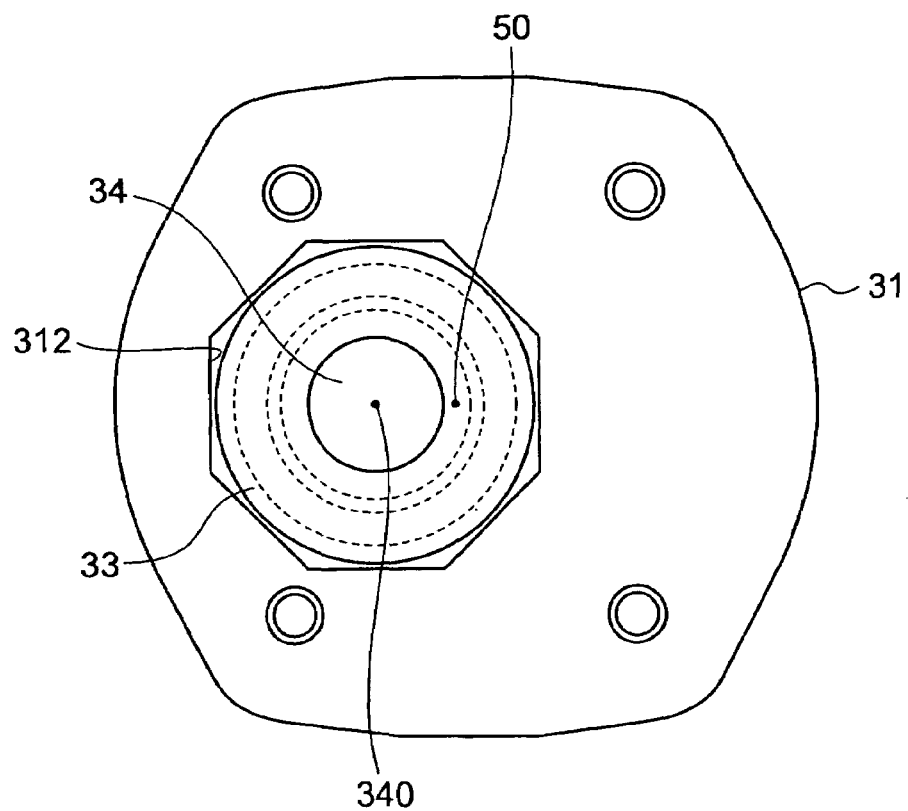
FIG. 4 is a plan view of the pulsation measuring unit of the wristwatch.

As shown in FIGS. 3 and 4, the pulsation measuring unit 3 includes a housing 31 to which the partition plate 15 is fixed, for example, by screws. The housing 31 has a substantially circular recess 311 whose center 340 is located at a position deviating somewhat from the center 50 of the housing 31. The bottom of the recess 311 has a through opening 312 and a ring-like groove 313 in which an O-like seal ring 32 is provided. A thin plate 33 is provided over substantially the whole recess 311 to thereby cover the opening 312.

The thin plate 33 is molded, for example, from a stainless steel (SUS) and thinner than the partition plate 15. The piezoelectric element 34 that acts as the sensor for sensing changes in the air pressure within the fluid chamber 5 and for converting them to an electric signal is bonded to an upper surface of the thin plate 33. As shown in FIG. 4, the piezoelectric element 34 is in substantially the form of a disc whose center 340 deviates from the center 50 of the fluid chamber 5.

The thin plate 33 has an electrically conductive pin 331 that connects electrically to the timepiece function unit 13 through the housing 31, partition plate 15 and support member 16. The piezoelectric element 34 has an electrically conductive pin 341 that electrically connects to the timepiece function unit 13 through the housing 31, partition plate 15 and support member 16. Thus, the electric pulsation sensed signal outputted by the piezoelectric element 34 is inputted through the pins 331 and 341 to the timepiece function unit 13.

A U-shaped spacer 35 is provided between the partition plate 15 and the thin plate 33 so as to form a space around the piezoelectric element 34. When pushed by the partition plate 15, the spacer 35 will press the thin plate 33 against the recess 313, thereby exerting a force on the O-shaped seal ring 32 such that airtightness is ensured between the upper- and lower-surface sides of the thin plate 33. Preferably, the spacer 35 is molded from a hard material such as acrylonitrile butadiene styrene resin (ABS) such that the partition plate 15 is not easily bent.

The bottom 39 of the fluid chamber 5 formed below the housing 31 is adapted to come into contact with the user's wrist W. The bottom 39 is comprised of an elastically deformable member 36 that will be deformed elastically by pulsation of blood in the blood tubes of the user's wrist transmitted from the band 2 to thereby change the air pressure within the fluid chamber 5, and a deformation preventing member 37 superposed on the outside of the deformable member 36 for preventing elastic deformation of the deformable member. The deformation preventing member 37 will come into contact with the user's wrist.

The deformable member 36 that partly composes the bottom of the fluid chamber 5 is pressed against the user's wrist W when the body of the wristwatch 100 is worn. The deformable member 36 is elastically deformable by pulsation of blood in the blood tubes of the user's wrist W and is preferably molded from urethane or silicon. The deformable member 36 comprises a fixing ring-like brim 361 fixed by a stop ring 4 to the case 1, and a downward projecting fluid-chamber part 362 whose bottom will come into contact with the user's wrist W. The brim 361 has a ring-like peripheral ridge 363 on the case side engaged in a corresponding recess 10 provided in the lower end of the case 1 when the deformable member 36 is fixed to the case 1, thereby positioning the deformable member 36 so as not to deviate from its proper position.

Figure 5:
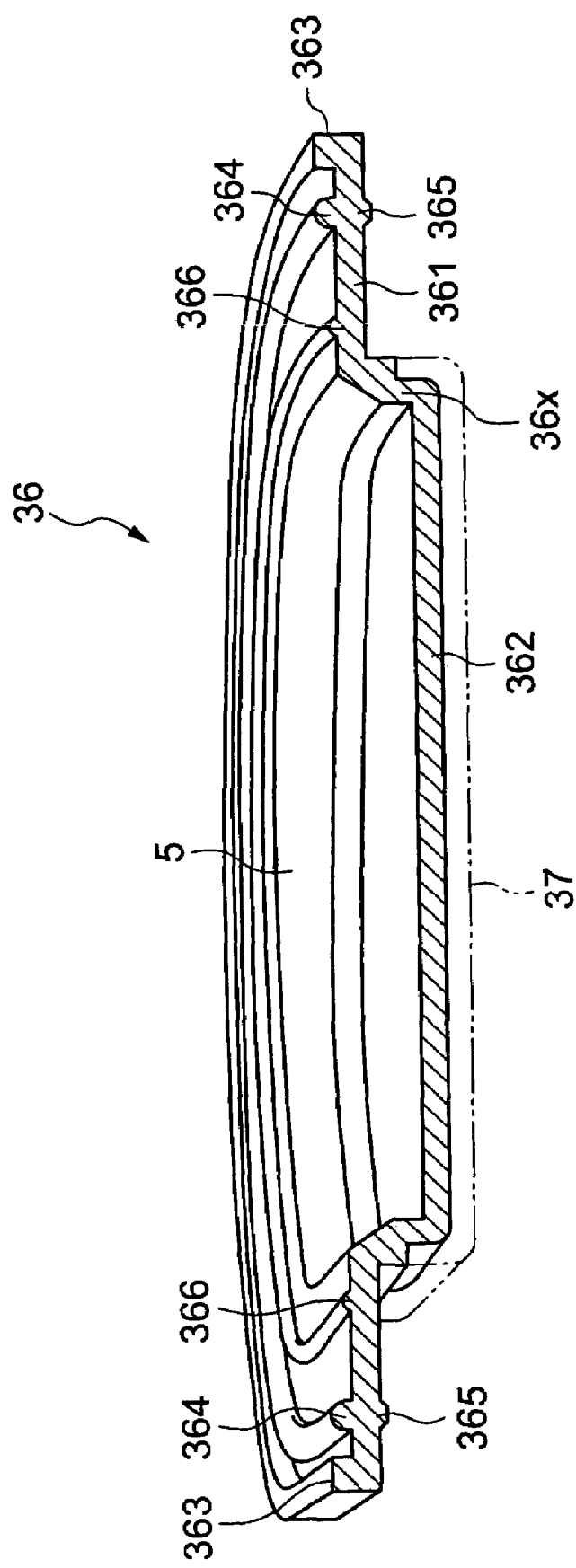
FIG. 5 is a perspective view of an elastically deformable member of the wristwatch.

As shown in FIG. 5, the brim 361 also has a first ring-like ridge 364 provided concentrically inside the ridge 363 thereon engaged in a corresponding recess provided in the case 1, and a second ring-like ridge 365 provided on the opposite side of the brim from the first ridge 364 and abutting on the stop ring 4. The brim 361 further comprises a third ridge 366 provided concentrically inside the first ridge 364 thereon and abutting on the case 1.

The housing 31 and the downward protruding deformable member 36 cooperate to form the fluid chamber 5 therebetween.

The deformation preventing member 37 is bonded by vulcanization to an outer surface of the fluid-chamber-bottom part 362 of the deformable member 36. The deformation preventing member 37 is molded from a hard material such as stainless steel (SUS) and prevents elastic deformation of the bottom part 362, thereby causing the pulsation transmitted from the user's wrist W to act uniformly on the bottom part 362.

The by-vulcanization bonding method may be either a direct by-vulcanization bonding method that comprises superimposing a rubber compound layer on a metal plate, and then vulcanizing both under pressure to thereby bond them together or an indirect by-vulcanization bonding method that comprises coating a metal plate with an adhesive, and then bonding both together.

As shown in FIG. 3, the stop ring 4 is molded from a hard material such as, for example, stainless steel (SUS) and is fixed to the brim 361 of the deformable member 36 with screws (not shown) to the case 1 to such an extent that the brim 361 is deformed slightly.

At this time, the first ridge 364 abutting on the case 1 is deformed to thereby ensure airtightness between the case 1 and the deformable member 36. The deformation of the second ridge 365 ensures airtightness between the stop ring 4 and the deformable member 36. The deformation of the third ridge 366 ensure airtightness between the housing 31 and the deformable member 36.

A method of measuring blood pulsation using the wristwatch 100 will be described next.

As shown in FIG. 2, when the body of the wristwatch 100 is worn on the back of the user's wrist W with the band 2, the band 2 is wound so as to extend in a direction perpendicular to the direction in which an ulna and a radius artery extend in the vicinity of the ulna S and radius T present within the user's forearm and positioned on the sides of the little and thumb fingers, respectively, of the user's hand.

The respective arteries repeatedly expand and shrink depending on changes in the pressure of blood being sent out from the user's heart in synchronism with his or her pulsation. When the artery expands, the band 2 receives an expanding force relative to the ulna and radius of the user's wrist. When the artery shrinks, the expanding force acting on the band 2 is released and the shrinking force acts on the band. Thus, the band 2 receives an expanding force and a relief from the expanding force alternately. These changes are transmitted to the pulsation measuring unit 3 through the band 2 and the case 1. Thus, when the artery expands, the tensile force acting on the band 2 is transmitted to the pulsation measuring unit 3, which is then pushed against the user's wrist W.

When the pulsation measuring unit 3 is pressed against the user's wrist W, the deformable member 36 is elastically deformed toward the inside of the case 1 through the deformation preventing member 37. Thus, the fluid chamber 5 formed between the deformable member 36 and the housing 31 is compressed. This increases the air pressure within the fluid chamber 5, which then presses and bends the thin plate 33 and hence the piezoelectric element 34 toward the housing 31. A voltage depending on the magnitude of the bending of the piezoelectric element 34 is produced in the piezoelectric element 34, and sent as an electric signal to the timepiece function unit 13, which counts the number of pulsations and displays it on the display 12.

According to the wristwatch 100 of the embodiment 1, the elastically deformable member 36 that constitutes the part of the wall 39 of the fluid chamber 5 is elastically deformed at the side parts 36x of the fluid chamber in accordance with blood pulsation produced in the blood tubes of the user's wrist W. Thus, the air pressure within the fluid chamber 5 changes. In this case, the bottom of the fluid of the chamber 5 made of the deformable member 36 is prevented from uneven elastic deformation due to the deformation preventing operation of the deformation preventing member 37 provided on the deformable member 36. Thus, the pressure changes within the fluid chamber 5 become uniform always. As a result, occurrence of undesirable vibration noise is restricted, thereby ensuring pulsation measurement with high accuracy.

The center 340 of the piezoelectric element 34 that senses changes in the pressure within the fluid chamber 5 and outputs a signal indicative of a result of its sensing to the pulsation measuring unit 3 deviates from the center 50 of the fluid chamber 5. Thus, when the pulsation is transmitted from the user's wrist W to the fluid chamber 5 through the band 2, the piezoelectric element 34 does not directly receive at its center the changes in the pressure within the fluid chamber 5. Thus, the piezoelectric element 34 can avoid suffering from changes in the fluid pressure within the fluid chamber 5 at its center. Accordingly, the piezoelectric element 34 can indirectly sense changes in the pressure within the chamber 5, thereby achieving pulsation measurement with high accuracy.

When the pulsation is transmitted to the deformable member 36 and the deformation preventing member 37 before being transmitted to the fluid chamber 5, the deformable member 36 tries to be elastically deformed due to the pulsation. On the other hand, the deformation preventing member 37 tries to prevent elastic deformation of the elastic deformable member 36. Thus, the deformable member 36 and the deformation preventing member 37 try to move away from each other, but they are fixed integrally to each other by vulcanization. Thus, the deformable member 36 is surely prevented from separating out from the pulsation preventing member 37.

Since the stop ring 4 that fixes the elastically deformable member 36 at its outer brim to the case 1, airtightness of the inside of the case 1 is ensured.

Since the case 1 has the timepiece function unit 13 and the display 12, it can also be used as a time display device in addition to as a pulsation sensing device.

Embodiment 2

An embodiment 2 of the wristwatch according to the present invention will now be described with reference to FIGS. 6 and 7.

Figure 6:
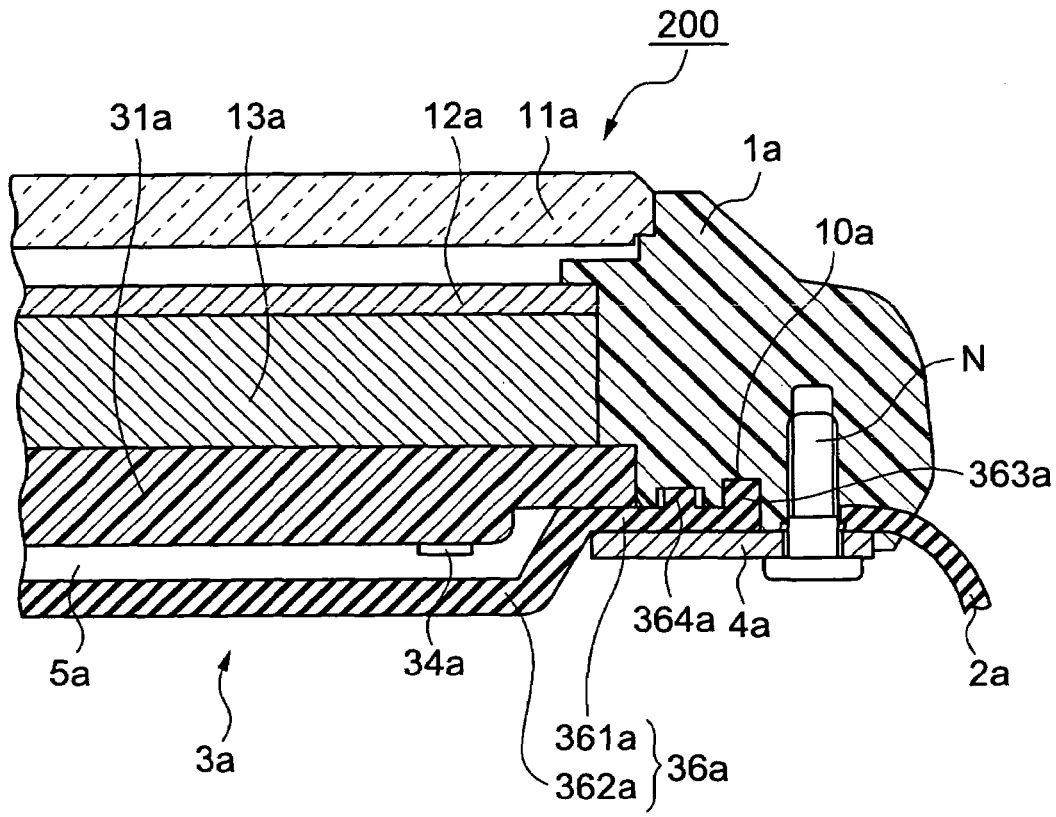
FIG. 6 is a fragmentary cross-sectional view of an embodiment 2 of the wristwatch.

As shown in FIG. 6, the wristwatch 200 comprises a body of the wristwatch and bands 2a by which the body of the wristwatch is worn on a user's wrist W. The body of the wristwatch comprises a case 1a, a timepiece function unit 13a housed within the case, and a pulsation measuring unit 3a that comprises a fluid chamber 5a provided on the user's wrist side of the case and a sensor that measures pulsation of blood in the blood tubes of the user's wrist by sensing changes in the air pressure within fluid chamber 5.

The case 1a is in substantially the form of a hollow cylinder with a crystal 11a fitted into an upper end thereof and with an elastically deformable member 36a fixed to a lower end thereof. The deformable member 36a will be elastically deformed in accordance with pulsation transmitted through the band 2a from the user's wrist W to thereby change the air pressure within the fluid chamber 5a. Provided within the case 1a are a timepiece function unit 13a, a housing 31a that fixes the timepiece function unit 13a within the case 1a and a display 12a that displays time information received from the timepiece function unit 13a. Preferably, the housing 31a is molded from a hard material such as acrylonitrile butadiene styrene resin (ABS) to ensure airtightness between the housing 31a and the deformable member 36a. A pressure sensor 34a is provided on a lower surface of the housing 31a to sense changes in the pressure within the fluid chamber 5a.

The case 1a has a ring-like recess 10a that is engaged with a corresponding ridge 363a provided on the deformable member 36a.

The bands 2a are used to wear the body of the wristwatch on the user's wrist W as well as transmit blood pulsation in the blood tubes of the user's wrist W to the deformable member 36a. The bands 2a are composed of a soft material elastically deformable depending on the pulsation transmitted from the user's wrist W. Preferably, the band material is a soft resin material such as urethane or silicon. The bands 2a are fixed at one end through the stop ring 4a by screws N to the corresponding sides of the case 1a.

The pulsation measuring unit 3a comprises the elastically deformable member 36a, a housing 31a, a pressure sensor 34a, and a fluid chamber 5a surrounded by the deformable member 36a and housing 31a.

Figure 7:
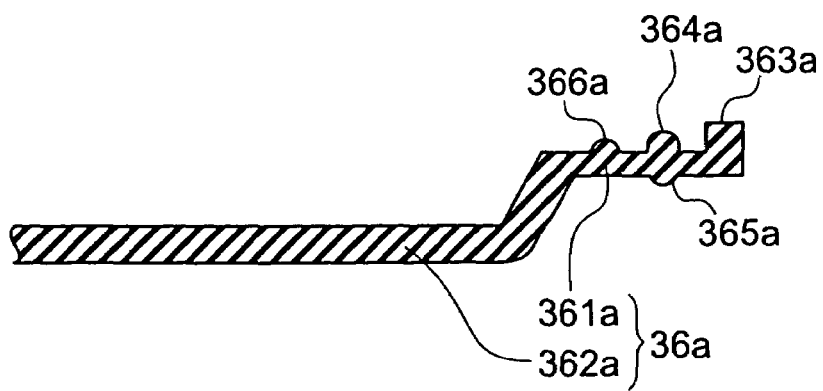
FIG. 7 is a fragmentary cross-sectional view of an elastically deformable member of the wristwatch of the embodiment 2.

As shown in FIG. 7, the deformable member 36a will come into contact with the user's wrist when the body of the wristwatch 200 is worn on the user's wrist. The deformable member 36a is molded from a soft material elastically deformed depending on the pulsation transmitted from the band 2a. The soft material is preferably urethane or silicon. As shown in FIGS. 6 and 7, the deformable member 36a comprises a ring-like fixing brim 361a that is fixed by the stop ring 4a to the case 1a and a lower part 362a protruding downward to thereby form a lower part of the fluid chamber whose bottom will come into contact with the user's wrist when the body of the wristwatch is worn. The ring-like fixing brim 361a has a ring-like peripheral ridge 363a provided on its case side such that when the brim 361a is fixed to the case 1a, the ring-like ridge 363a is engaged in a corresponding recess 10a on the case 1a, thereby positioning the deformable member 36a so as not to deviate from its proper position.

The fixing brim 361a further includes a first ring-like ridge 364a formed thereon inside the peripheral ridge 363a and received in a corresponding recess in the case 1a. The fixing brim 361a further includes a second ring-like ridge 365a provided on the opposite side of the fixing brim 361a from the first ridge 364a and abutting on the stop ring 4a. Further, the fixing brim 361a includes a third ring-like ridge 366a inside the first ridge 364a abutting on the housing 31a.

The lower part 362a and the housing 31a cooperate to form a sealed fluid chamber 5a there between.

The stop ring 4a is molded from a hard material such as, for example, stainless steel (SUS). The stop ring 4a fixes the brim 361a of the deformable member 36a and the band 2a with screws N to the case 1a such that the deformable 36a is slightly deformed in a pressed down manner.

At this time, the first ridge 364a abutting on the case 1a is deformed such that air tightness between the case 1a and the deformable member 36a is ensured. When the second ridge 365a is deformed, air tightness between the stop ring 4a and the deformable member 36a is ensured. In addition, when the third ridge 366a is deformed, air tightness between the housing 31a and the deformable member 36a is ensured. When the body of the wristwatch 200 is worn on the user's wrist for measuring purposes, the deformable member 36a is elastically deformed into the case 1a by blood pulsation produced in the user's wrist, and the fluid chamber 5a formed between the housing 31a and the deformable member 36a is compressed. This increases the air pressure within the fluid chamber 5a and the increased pressure is sensed by the pressure sensor 34a.

According to the wristwatch 200 of the embodiment 2, the elastically deformable member 36a is molded from a material being elastically deformed depending on pulsation from the user's wrist W on which the body of the wristwatch 200 is worn. Thus, fitness and pleasant texture of the wristwatch to the user's wrist is maintained well. In addition, a soft member need not be provided superimposed on the deformable member 36a as in the prior art, thereby preventing the wristwatch 200 from thickening. It is considered that forming the deformable member 36a from the soft material may raise a problem of air tightness of the inside of the case 1a. However, the ridge 363a provided on the fixing brim 361a of the deformable member 36a is engaged in the corresponding recess 10a in the case 1a, so that although the deformable member 36a is molded from a soft material, the deformable member 36a does not deviate from its proper position, thereby ensuring the air tightness of the inside of the case 1a.

The ridge 363a is in the form of a ring extending along the periphery of the brim of the deformable member 36a to thereby maintain the air tightness of the inside of the case 1a at high level.

The first ridge 364a provided on the fixing brim 361a abuts on the case 1a to thereby improve air tightness. The second ridge 365a abuts on the stop ring 4a to increase air tightness. Thus, air tightness of the inside of the case 1a is improved. The wristwatch 200 also counts the number of pulsations based on the changes in the air pressure within the fluid chamber 5a and informs the user of the number of pulsations counted. Thus, the number of pulsations can be easily obtained in a very simple method without wearing a cuff.

The stop ring 4a that fixes the deformable member 36a at its brim to the case 1 is provided, thereby ensuring air tightness of the inside of the case 1a.

Since the case 1a includes the timepiece function unit 13a and the display 12a, it can be used as the pulsation sensor as well as the time display device.

Embodiment 3

An embodiment 3 of the wristwatch according to the present invention will be described with reference to FIG. 8. The embodiment 3 has the same structure as the embodiment 2 except that the fixing brim 361b and the lower part 362b of the deformable member 36b of the pulsation measuring unit 3b are molded from different materials. Thus, the points at which the embodiment 3 is different from the embodiment 2 will be mainly described, and further description of the embodiment 3 will be omitted.

Figure 8:
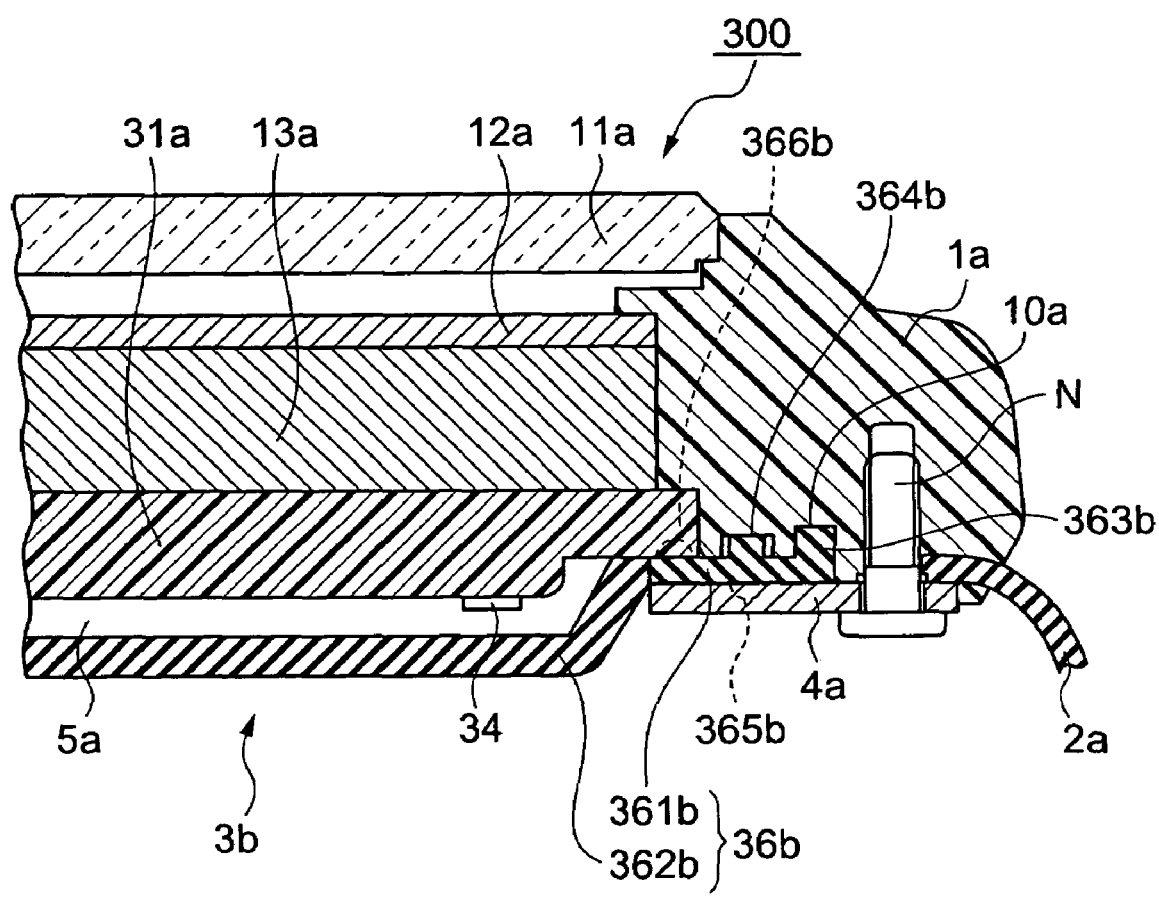
FIG. 8 is a fragmentary cross-sectional view of an embodiment 3 of the wristwatch.

As shown in FIG. 8, the elastically deformable member 36b of the wristwatch 300 comprises a fixing brim 361b that is pushed down by a stop ring 4a against the case 1a, and a lower part 362b protruding outward. The fixing brim 361b is molded from a material having a lower elasticity than the lower part 362b such as, for example, denatured silicon urethane or urethane rubber. The ring-like fixing brim 361b has a ring-like peripheral ridge 363b provided on its case side such that when the brim 361b is fixed to the case 1a, the ring-like ridge 363b is engaged in a corresponding recess 10a on the case 1a, thereby positioning the deformable member 36b so as not to deviate from its proper position.

The fixing brim 361b further includes a first ring-like ridge 364b formed thereon inside the peripheral ridge 363b and received in a corresponding recess in the case 1a. The fixing brim 361b further includes a second ring-like ridge 365b provided on the opposite side of the fixing brim 361b from the first ridge 364b and abutting on the stop ring 4a. Further, the fixing brim 361b includes a third ring-like ridge 366b inside the first ridge 364b abutting on the housing 31a.

At this time, the first ridge 364b abutting on the case 1a is deformed such that air tightness between the case 1a and the deformable member 36b is ensured. When the second ridge 365b is deformed, air tightness between the stop ring 4a and the deformable member 36b is ensured. In addition, when the third ridge 366b is deformed, air tightness between the housing 31a and the deformable member 36b is ensured. The lower part 362b is molded from an environment-resistant material such as, for example, urethane that has resistance to predetermined environmental factors such as the temperature and humidity of a space present around the lower part 362b, substances adhering to the lower part 362b or ultraviolet rays. The lower part 362b is provided so as to be spaced away from the housing 31a to thereby form the fluid chamber 5a there between.

The wristwatch 300 of the embodiment 3 produces advantageous effects similar to those produced by the embodiment 2. In addition, when the fixing brim 361b is fixed by the stop ring 4a, a force repelling the pressing force is small. Thus, the stop ring 4a maintains the fixing brim 361b in a pressed state, thereby maintaining the air tightness of the inside of the case 1a. Since the lower part 362b exhibits resistance to changes in the environment, the durability of the deformable member 36b is improved.

Embodiment 4

An embodiment 4 of the wristwatch according to the present invention will be described with reference to FIG. 9. The embodiment 4 has the same structure as the embodiment 2 excluding that the wristwatch 400 of the embodiment 4 comprises a pulsation measuring unit 3c equal in composition to the pulsation measuring unit 3 of the embodiment 1 and a deformation preventing member 37d is fitted into the inside of the lower part 362c. Thus, the points where the embodiment 4 is different from the embodiment 2 will be mainly described and further description of the embodiment 4 will be omitted.

Figure 9:
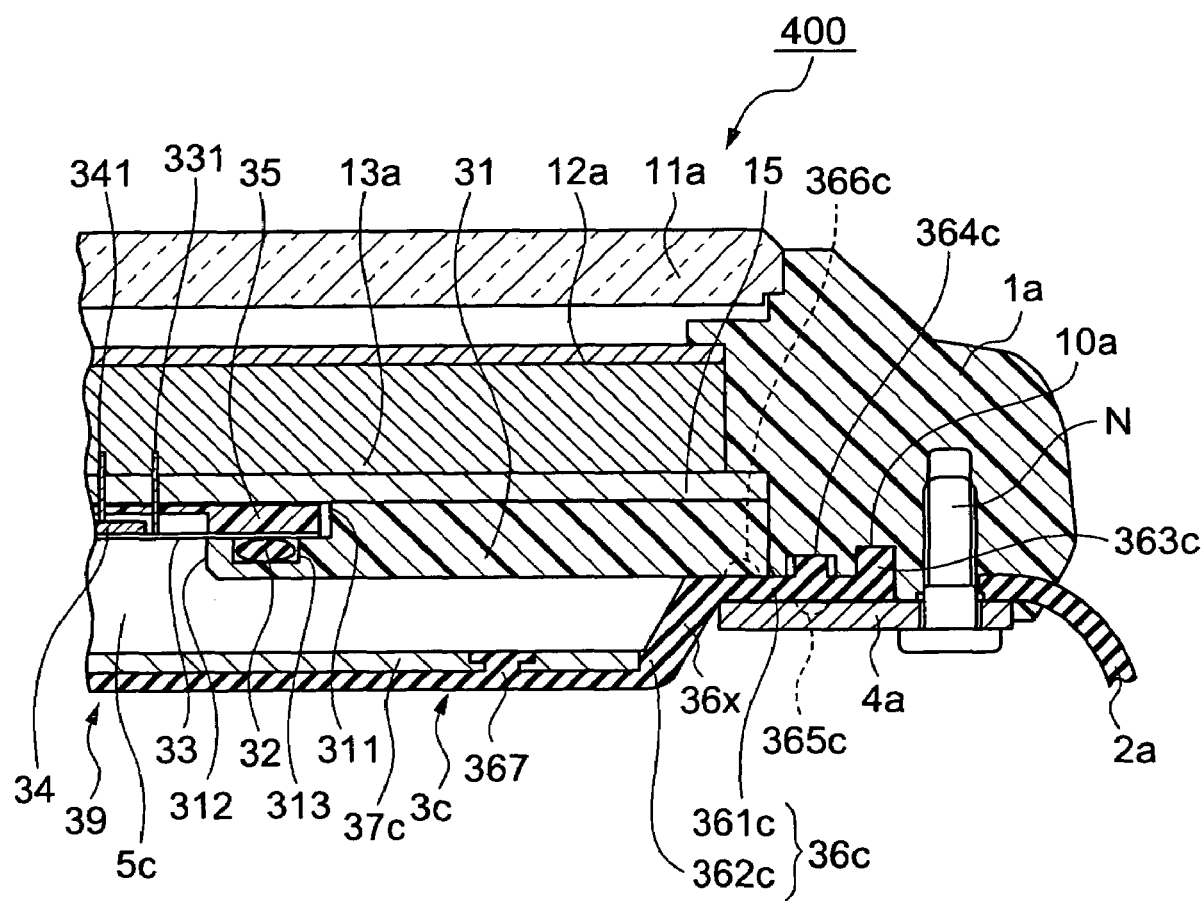
FIG. 9 is a fragmentary cross-sectional view of an embodiment 4 of the wristwatch.

As shown in FIG. 9, a partition plate 15 is provided that partitions a space within the case 1a is provided on a lower surface of the timepiece function unit 13a, for example, of SUS, and the pulsation measuring unit 3c is provided on a lower surface of the partition plate 15.

An elastically deformable member 36c that covers the inside of the case 1a and will be elastically deformed by pulsation being transmitted through the band 2a, thereby changing the air pressure within the fluid chamber 5c is provided below the housing 31.

The deformable member 36c comes into contact with the user's wrist W when the body of the wristwatch 400 is worn on the user's wrist. The deformable member 36c is molded from a soft material being elastically deformed depending on pulsation of blood in the blood tubes of the user's wrist. The soft material is preferably urethane or silicon. The deformable member 36c comprises a ring-like fixing brim 361c that is fixed by a stop ring 4a to the case 1a and a protruding downward lower part 362c coming into contact with the user's wrist on which the body of the wristwatch is worn. The ring-like fixing brim 361c has a ring-like peripheral ridge 363c provided on the case side engaged in a corresponding recess 10a in the case 1a when the brim 361c is fixed to the case 1a, thereby positioning the deformable member 36c so as not to deviate from its proper position.

The fixing brim 361c further includes a first ring-like ridge 364c formed thereon inside the peripheral ridge 363c on the case side and received in a corresponding recess in the case 1a. The fixing brim 361c further includes a second ring-like ridge 365c provided on the opposite side of the fixing brim 361c from the first ridge 364c and abutting on the stop ring 4a. Further, the fixing brim 361c includes a third ring-like ridge 366c inside the first ridge 364c abutting on the housing 31.

The housing 31 and the lower part 362c protruding downward from the housing 31 form a fluid chamber 5c there between.

A deformation preventing member 37c that prevents the lower part 362c from being elastically deformed is bonded by vulcanization to the inside of the lower part 362c. The deformation preventing member 37c is molded from a hard material such as SUS and causes the pulsation being transmitted from the user's wrist to act evenly to the lower part 362c. The deformation preventing member 37c is molded integral with the lower part 362c in such a manner that lugs 367 on the exposed member 362c are engaged in holes in the deformation preventing member 37c. The exposed member 362c and the deformation preventing member 37c form a wall of the fluid chamber 5c on the user's wrist side.

The embodiment 4 of the wristwatch 400 produces advantageous effects similar to those produced by the embodiments 1 and 2. In addition, the deformation preventing member 37c is fixed to the inside of the lower part 362c. Thus, it will not touch the user's wrist even when the body of the wristwatch is worn on the user's wrist, and maintains fitness and pleasant texture of the wristwatch to the user while improving the strength and rigidity of the wristwatch 400. When the deformable member 36c is pressed, the resulting force will press the whole deformation preventing member 37c. Thus, a change rate of the volume of a space formed between the formable member 36c and the housing 31 and hence the sensitivity of the piezoelectric element 34 is improved.

Embodiment 5

An embodiment 5 of the wristwatch according to the present invention will be described with reference to FIG. 10. The embodiment 5 has the same structure as the embodiment 4 excluding that the wristwatch 500 of the embodiment 5 comprises a deformation preventing member 37d fitted to the inside of the lower part 362d to reinforce the lower part 362d and prevent elastic deformation of the lower part 362d. Thus, the points at which the embodiment 5 is different from the embodiment 4 will be mainly described and further description of the embodiment 5 will be omitted.

Figure 10:
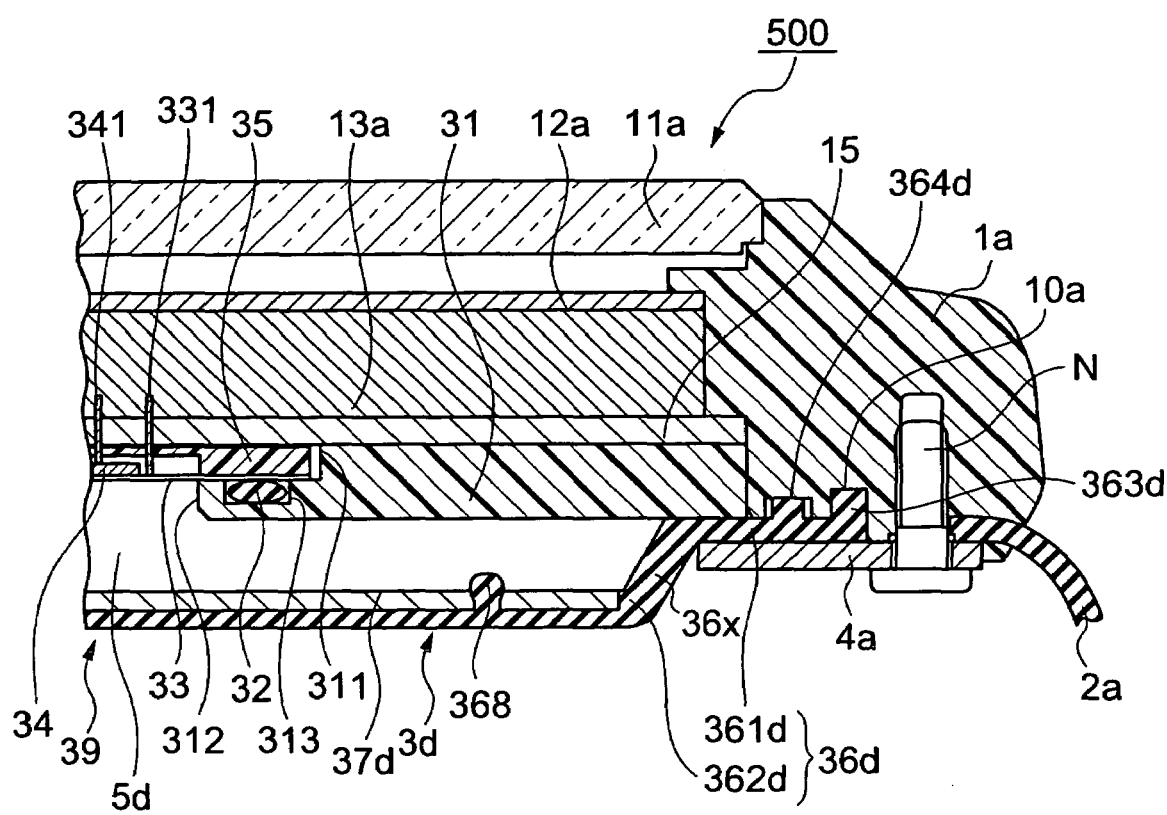
FIG. 10 is a fragmentary cross-sectional view of an embodiment 5 of the wristwatch.

As shown in FIG. 10, the elastic deformable member 36d of the wristwatch 500 is fixed to the deformation preventing member 37d provided on the inner surface thereof in such a manner that lugs 368 provided on the inside of the lower part 362d are press fitted into corresponding holes provided in the deformation preventing member 37d molded from a hard material such as, for example, stainless steel (SUS). The lower part 362d may be bonded to the deformation preventing member 37d by vulcanization.

The wristwatch 500 of the embodiment 5 produces advantageous effects similar to those produced by the embodiment 4. In addition, the deformation preventing member 37d and the part 362d of the deformable member 36d corresponding to the bottom of the fluid chamber are molded integrally. Thus, no work such as bonding the deformation prevention member 37d and the deformable member part 362d with an adhesive by hand and then bonding both together by hand is needed. Hence, man-hour is reduced and productivity of the apparatuses is increased.

Embodiment 6

An embodiment 6 of the wristwatch according to the present invention will be described with reference to FIG. 11. The embodiment 6 has the same structure as the embodiment 5 except that a space is provided between the lower part 362d and the deformation preventing member 27d with an announciator 6 provided in the space on the deformation preventing member 27d. Thus, the points where the embodiment 6 is different from the embodiment 5 will be mainly described and further description of the embodiment 6 will be omitted.

Figure 11:
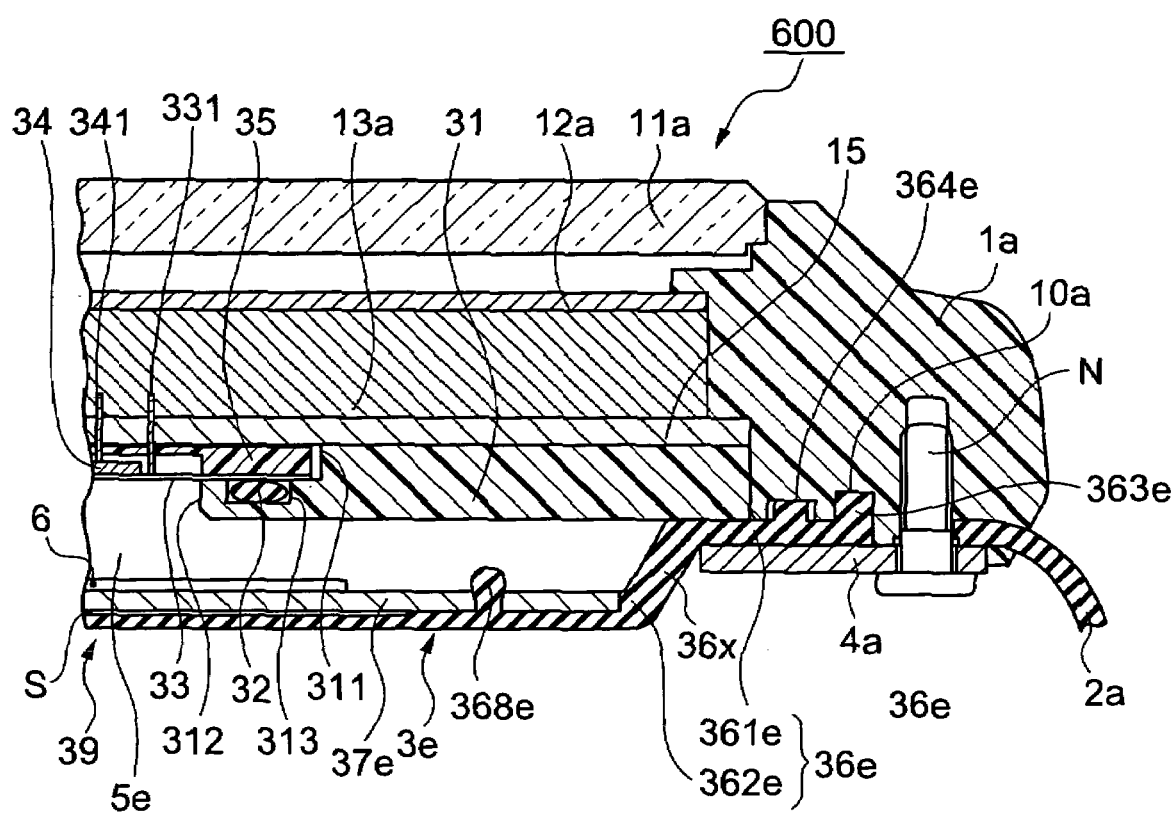
FIG. 11 is a fragmentary cross-sectional view of an embodiment 6 of the wristwatch.

As shown in FIG. 11, the elastic deformable member 36e of the wristwatch 600 is fixed to the deformation preventing member 37e provided on the inner surface thereof in such a manner that lugs 368e provided on the inside of the lower part 362e are press fitted into corresponding holes provided on the deformation preventing member 37e made of a hard material, for example, of SUS. A side of the lower part 362e placed in contact with the deformation preventing member 37e is removed partly so as to form a space S there between. An annunciate 6 is provided on the deformation preventing member 37e above the space S.

The annunciate 6 may comprise, for example, an FM sound source, a high-fidelity sound source MIDI sound source or a PCM sound source for the wristwatch.

The wristwatch 600 of the embodiment 6 produces advantageous effects similar to those produced by the embodiment 5. In addition, since the deformation preventing member 37e is provided partly spaced from the lower part 362e, the deformation preventing member 37e is capable transmitting sound from the annunciate 6 to the outside without absorbing vibrations of the deformation preventing member 37e.

Embodiment 7

An embodiment 7 of the wristwatch according to the present invention will be described with reference to FIG. 12. The embodiment 7 of the wristwatch according to this invention has the same structure as the embodiment 2 excluding that the deformation preventing member is provided outside the lower part 362f of the deformable member 36f. Thus, the points where the embodiment 7 is different from the embodiment 2 will be mainly described and further description of the embodiment 7 will be omitted.

Figure 12:
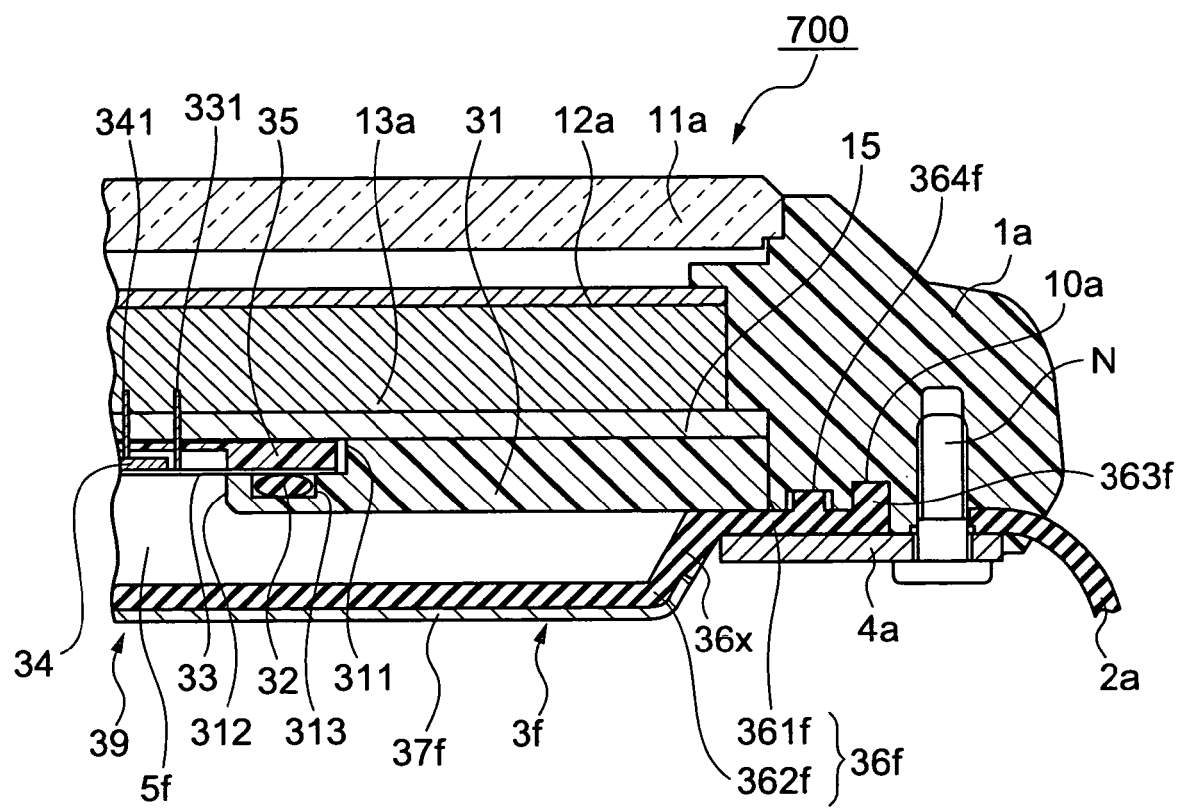
FIG. 12 is a fragmentary cross-sectional view of an embodiment 7 of the wristwatch.

As shown in FIG. 12, a portion of the lower part 362f of the wristwatch 700 has a hollow of a depth equal to the thickness of the deformation preventing member 37e on its outer surface thereof in which hollow the deformation preventing member 37f is bonded by the vulcanization. The deformation preventing member 37f is molded from a hard material such as stainless steel (SUS).

The wristwatch 700 of the embodiment 7 produces advantageous effects similar to those produced by the embodiments 4 and 5. In addition, in the embodiment 7 the deformation preventing member 37f fixed to the outer surface of the lower part 362f prevents the deformable member 36f from directly getting an external shock and coming into contact with an external object. Since no deformation preventing member is provided except on the lower part 362f, the lower part 362f itself is allowed to be elastically deformed while preventing the deformation preventing member 36f bonded to the inside of the deformation preventing member 37f from being cracked.

Embodiment 8

An embodiment 8 of the wristwatch according to the present invention will be described with reference to FIG. 13. The embodiment 8 has the same structure as the embodiment 7 excluding that the stop ring 4g is superposed on the brim of the deformation preventing member 37g. Thus, the points where the embodiment 8 is different from the embodiment 7 will be mainly described and further description of the embodiment 8 will be omitted.

Figure 13:
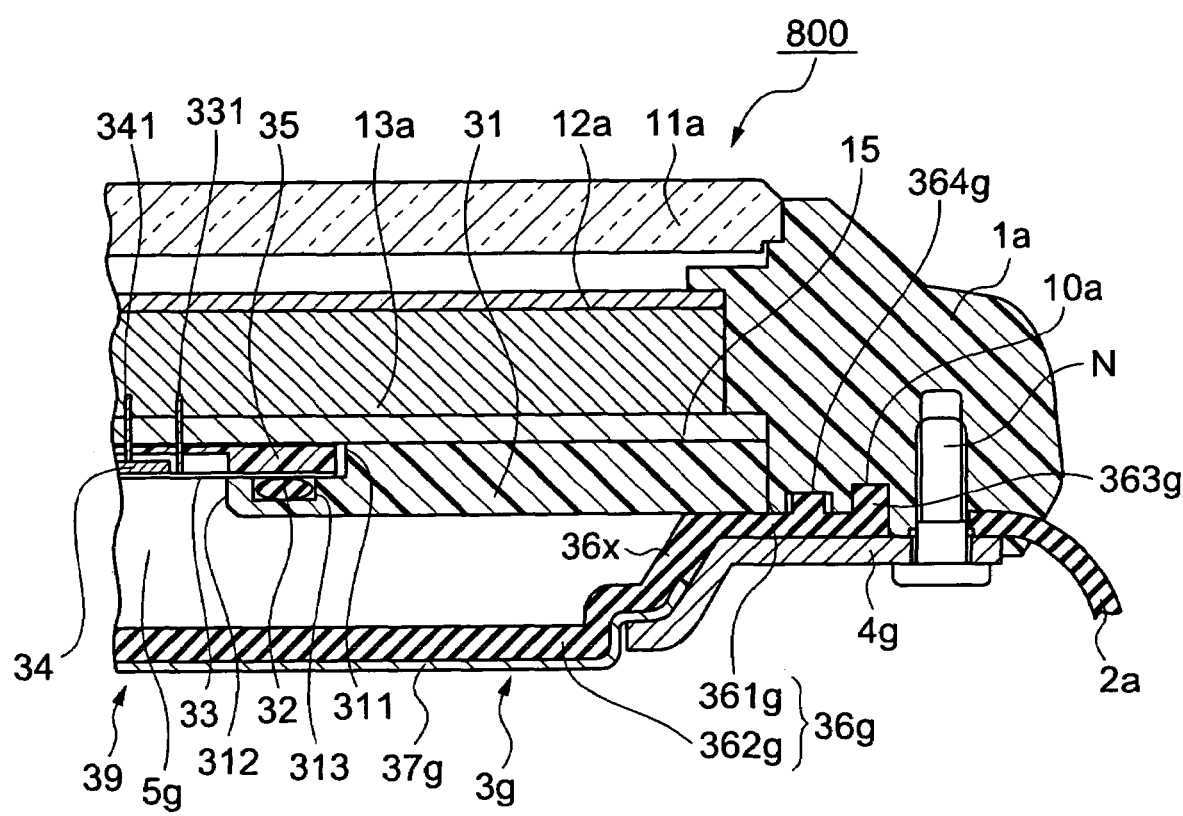
FIG. 13 is a fragmentary cross-sectional view of an embodiment 8 of the wristwatch.

As shown in FIG. 13, the lower part 362g of the deformable member 36g of the wristwatch 800 has a hollow of a depth equal to the thickness of the deformation preventing member 37g on the outer surface thereof in which hollow the deformation preventing member 37g is bonded to the part 362g by vulcanization. The deformation preventing member 37g is molded from a hard material such as stainless steel (SUS). The stop ring 4g that fixes the fixing brim 361g to the case 1a extends so as to cover the sidewall of the deformation preventing member 37g. The brim and sidewall of the deformation preventing member 37g is covered by, but not bonded to, the stop ring 4g. Thus, when the deformable member 36g is deformed elastically, the deformation preventing member 37g provided on the deformable member 36g moves in accordance with elastic deformation of the deformable member 36g, but the stop ring 4g does not move.

The wristwatch 800 of the embodiment 8 produces advantageous effects similar to those produced by the embodiment 7. In addition, since the stop ring 4g is superposed on the brim of the deformation preventing member 37g, the lower part 362g of the deformable member is completely covered by the deformation preventing member 37g or the stop ring 4g. Thus, the deformation preventing member 37g or stop ring 4g undertakes getting an external shock or direct contact with an external object, thereby reducing the possibility of the deformation preventing member 37g being cracked. The deformation preventing member 37g is completely covered, but no deformation preventing member 37g is provided except on the lower part 362g. In addition, the deformation preventing member 37g is not bonded to the stop ring 4g. Thus, the lower part 362g itself is allowed to be deformed elastically while preventing the deformable member 36g present on the inside of the deformation preventing member 37g from being cracked.

Embodiment 9

An embodiment 9 of the wristwatch according to the present invention will be described with reference to FIG. 14. The embodiment 9 has the same structure as the embodiment 2 excluding that a part of the deformable member 36a is replaced with a hard material fixed to the case 1a and that no stop ring is used. Thus, the points where the embodiment 9 is different from the embodiment 2 will be mainly described and further description of the embodiment 9 will be omitted.

Figure 14:
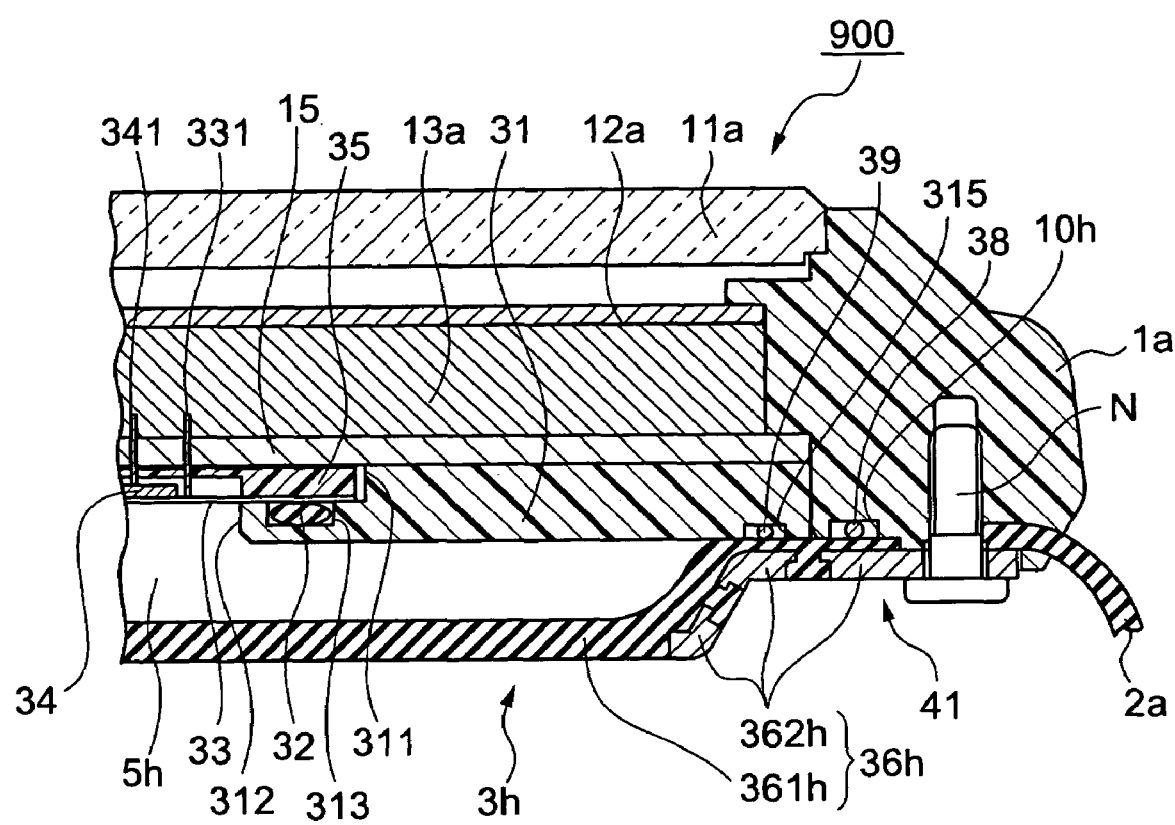
FIG. 14 is a fragmentary cross-sectional view of an embodiment 9 of the wristwatch.

As shown in FIG. 14, the deformable member 36h of wristwatch 900 comprises a soft part 361h that is elastically deformable by a force exerted from the user's wrist on which the body of the wristwatch 900 proper is worn, and hard parts 362h integral with the soft part 361h and made of a harder material than the soft part 361h as the fixing brim 41 pressed against the case 1a. The soft part 361h is molded, for example, from urethane or silicon. The hard part 362h is molded, for example, from a metal material such as stainless steel (SUS) or a resin such as acrylonitirile butadiene styrene. Further, hard parts 362h are also provided and used as reinforcements at bends of the deformable member 36h. The fixing brim 41 is attached by screws N to the case 1a.

An O-like seal ring 38 is provided in a corresponding recess 10h in a lower end of the case 1a that is in contact with the soft part 361h of the deformable member 36h. A second O-like seal ring 39 is provided in a corresponding recess 315 provided in a lower end of the peripheral portion of the housing 31 that is in contact with the soft part 361h of the deformable member 36h. The soft part 362h of the deformable member 36h is pressed against the case 1a and the housing 31 such that the O-like seal rings 38 and 39 are deformed in the corresponding recesses 10h and 315, respectively, for airtight purpose.

According to the wristwatch 900 of the embodiment 9, the deformable member 36h comprises the soft part 362h. Thus, fitness and pleasant texture of the deformable member 36h to the user's wrist are maintained and no more soft members such as a cuff need be provided in a superimposed state on the deformable member 36h, thereby preventing the apparatus from thickening. No members that push the deformable member 36h against the case 1a are needed. Thus, the number of parts is reduced, and the apparatus is reduced in weight and size.

In addition, the hard and soft parts 362h and 361h are molded integrally. Thus, no work such as bonding the hard and soft parts 362h and 361h with an adhesive by hand and then bonding both together by hand is needed. Hence, man-hour is reduced and productivity of the apparatuses is increased.

Embodiment 10

An embodiment 10 of the wristwatch according to the present invention will be described with reference to FIG. 15. The embodiment 10 has the same structure as the embodiment 9 except that airtight ridges are provided on the deformable member 36h instead of O-like seal rings such as shown by 38 and 39. Thus, the points where the embodiment 10 is different from the embodiment 9 will be mainly described and further description of the embodiment 10 will be omitted.

Figure 15:
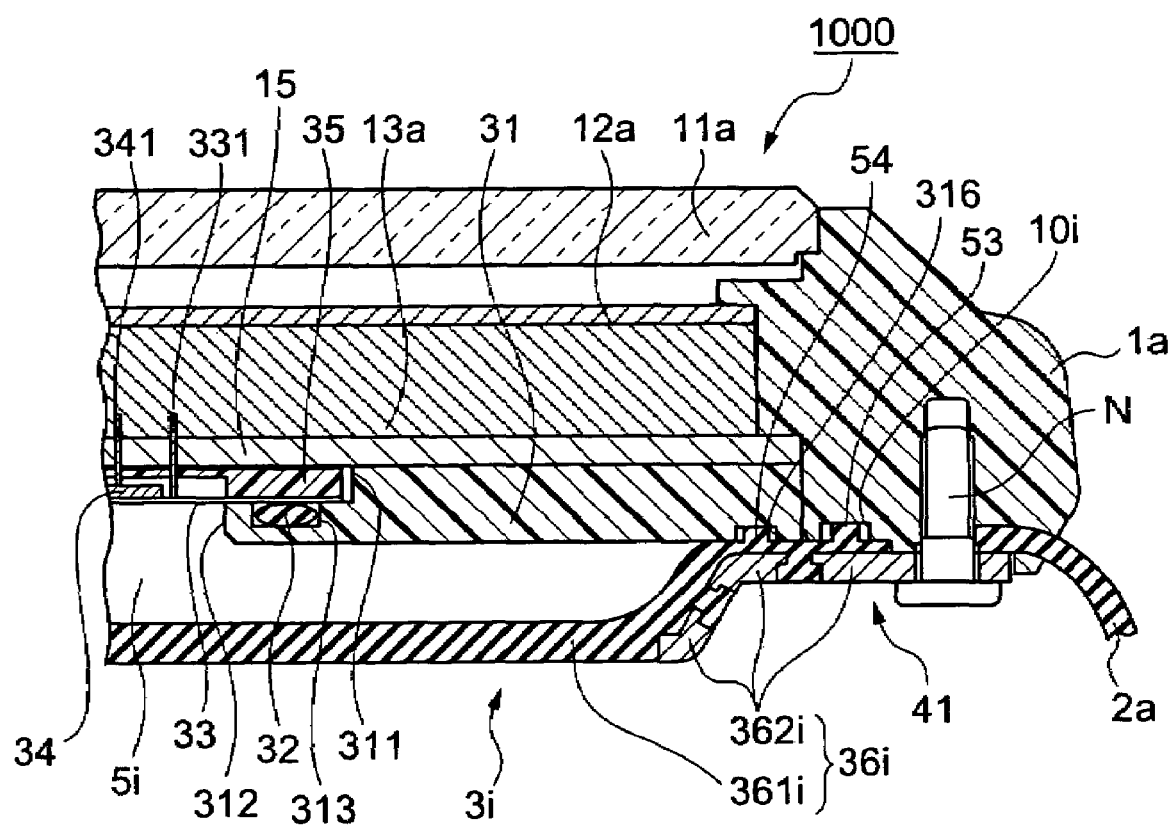
FIG. 15 is a fragmentary cross-sectional view of an embodiment 10 of the wristwatch.

As shown in FIG. 15, the soft part 361i of the deformable member 36i of the wristwatch 1000 has a ring-like airtight ridge 53 provided on the case side engaged in a corresponding recess 10i provided on the case 1a. The soft part 361i also has a second airtight ridge 54 on the housing side provided concentric with the ridge 53 and engaged in a corresponding recess 316 provided on the housing 31. The airtight ridges 53 and 54 are pressed against the case 1a and housing 31, respectively, such that the ridges 53 and 54 are deformed to expand in the recesses 10i and 316, respectively, for airtight purpose.

The embodiment 10 of the wristwatch 1000 produces advantageous effects similar to those produced by the embodiment 9. In addition, the deformable member 36i of the embodiment 10 is difficult to deviate compared to the embodiment 9.

Embodiment 11

An embodiment 11 of the wristwatch according to the present invention will now be described with reference to FIGS. 16 and 17. The embodiment 11 has the same structure as the second embodiment 2 except that a first ring-like ridge 11j provided at a position on the case 1a of the embodiment 1 corresponding to the position of the recess 10a on the case 1a of the embodiment 2 is engaged in a first corresponding recess 363j provided at a position on the deformable member 36j of the embodiment 11 corresponding to the position of the ridge 363a of the deformable member 36d of the embodiment 11; a second ridge 12j provided at the position on the case 1a is engaged in a second ring-like recess 364j provided at a position on the deformable member 36j of the embodiment 11 corresponding to the position of the first ridge 364a of the deformable member 36a of the embodiment 2; and a ring-like ridge 365j provided on the stop ring 4j on the side of the deformable-member fixing brim 361j is engaged in a ring-like recess 365i provided on the fixing brim 361j of the deformable member 36j. The points where the embodiment 11 different from the embodiment 2 will be mainly described and further description of the embodiment 11 will be omitted.

Figure 16:
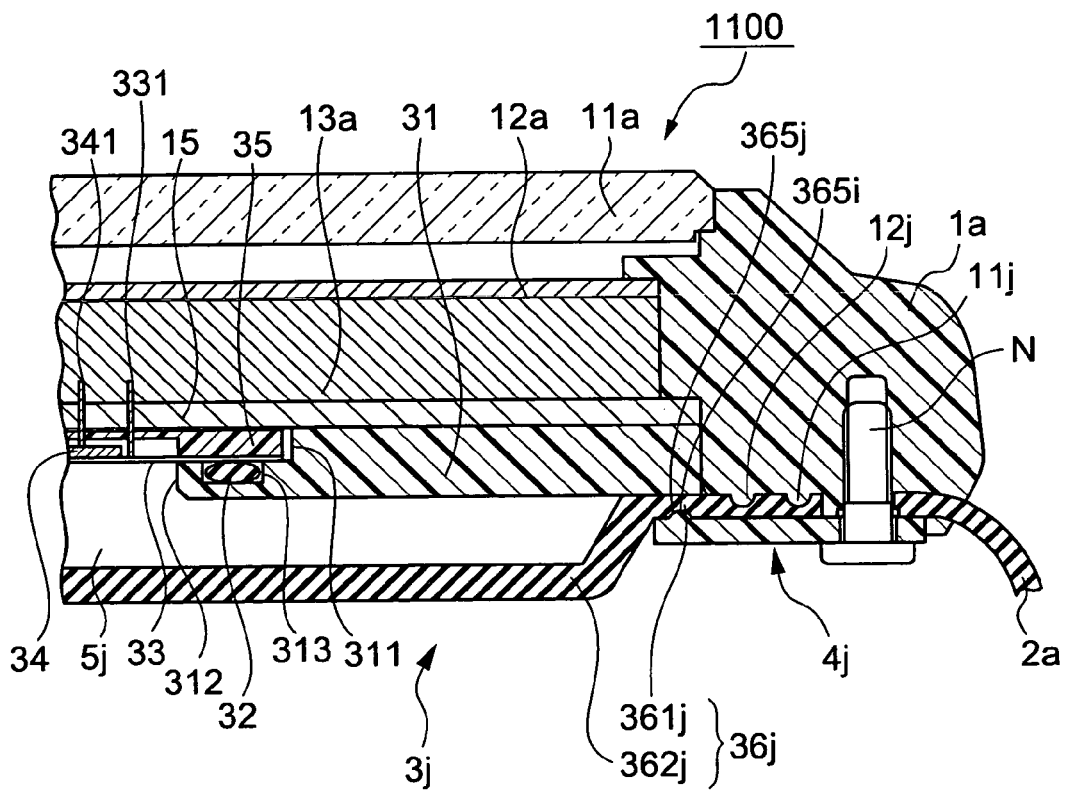
FIG. 16 is a fragmentary cross-sectional view of an embodiment 11 of the wristwatch.
Figure 17:
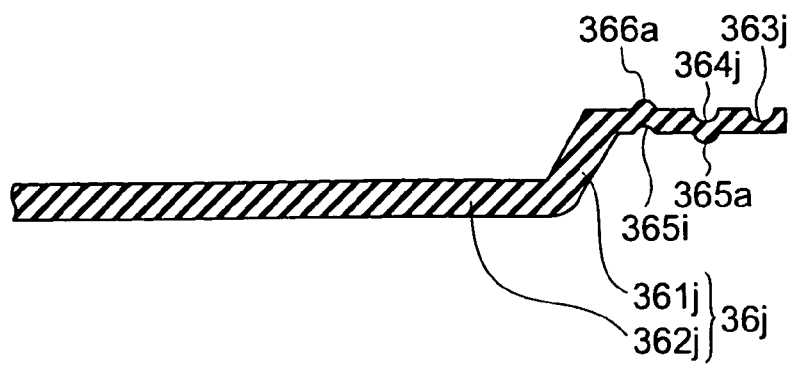
FIG. 17 is a fragmentary cross-sectional view of an elastically deformable member of the wristwatch of the embodiment 11.

As shown in FIGS. 16 and 17, the case 1a of the wristwatch 1100 has the first ring-like ridge 11j that is engaged in a corresponding ring-like recess 363j provided on the fixing brim 361j of the deformable member 36j for positioning purpose.

The case 1a also has a second ring-like ridge 12j inside the first ridge 11j engaged in a second corresponding recess 364j in the brim 361j of the deformable member 36j for positioning purpose.

The stop ring 4j has a ring-like ridge 365j thereon engaged in a corresponding recess 365i provided on the brim 361j of the deformable member 36j for positioning purpose.

The wristwatch 1100 of the embodiment 11 produces advantageous effects similar to those produced by the embodiment 2. In addition, the inside of the case 1a is covered by the deformable member 36j. When the fixing flange 361j of the deformable member 36j is pushed by the stop ring 4j, the first ridge 11j is engaged in the first recess 363j to ensure airtightness of the case 1a inside. The ridges 12j and 365j are engaged in the recesses 364j and 365i, respectively, to thereby position the deformable member 36j in position relative to the case 1a. Since the soft-material deformable member 36j in which the recess 365i is formed does not deviate, the airtightness of the case 1a inside is maintained.

Embodiment 12

An embodiment 12 of the wristwatch according to the present invention will be described with reference to FIGS. 18 and 19. The embodiment 12 has the same structure as the embodiment 4 except that the deformable member 36a is molded integral with the band 2a. The points where the embodiment 12 is from the embodiment 4 will be mainly described and further description of the embodiment 12 will be omitted.

Figure 18:
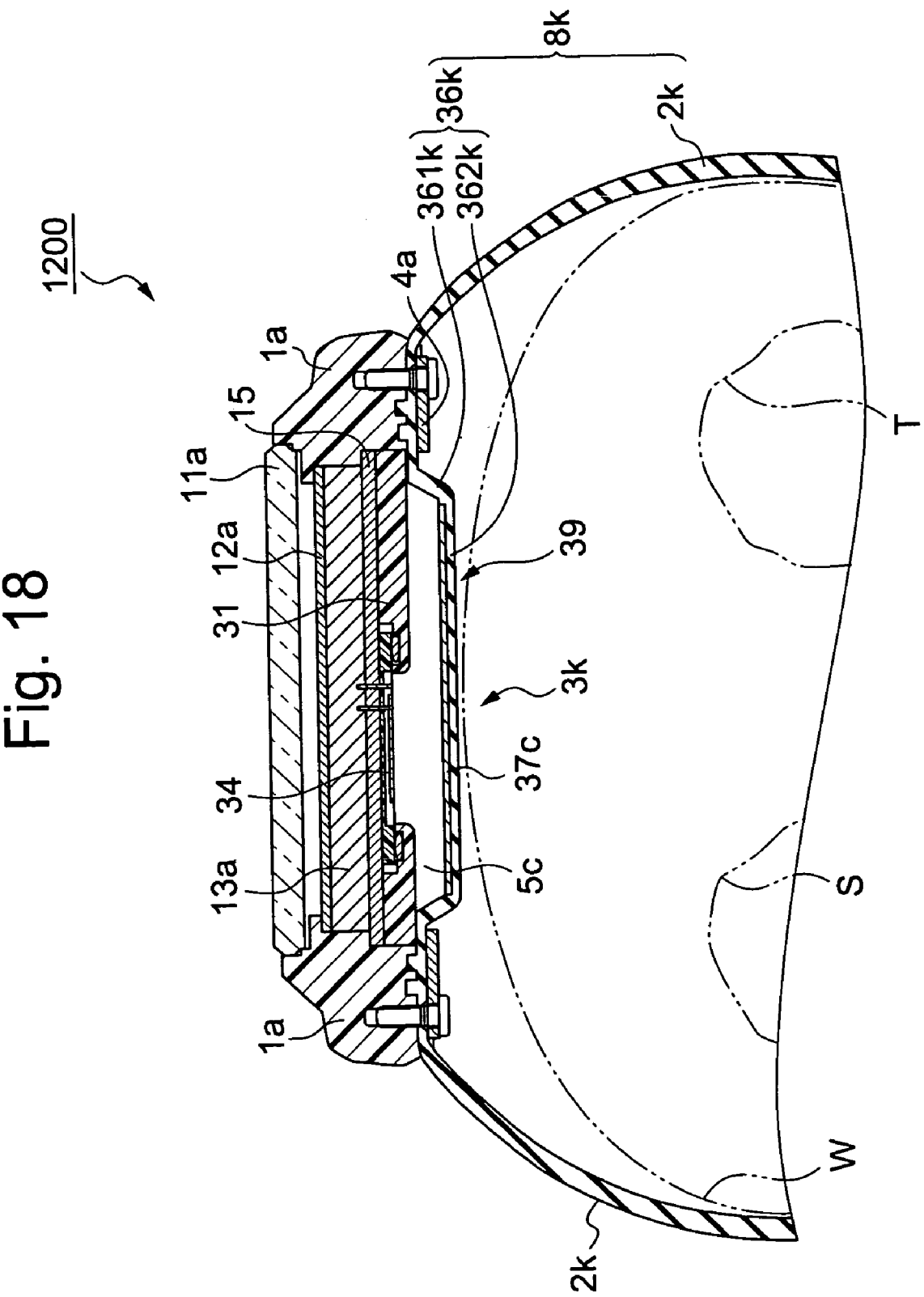
FIG. 18 is a cross-sectional view of an embodiment 12 of the wristwatch.
Figure 19:
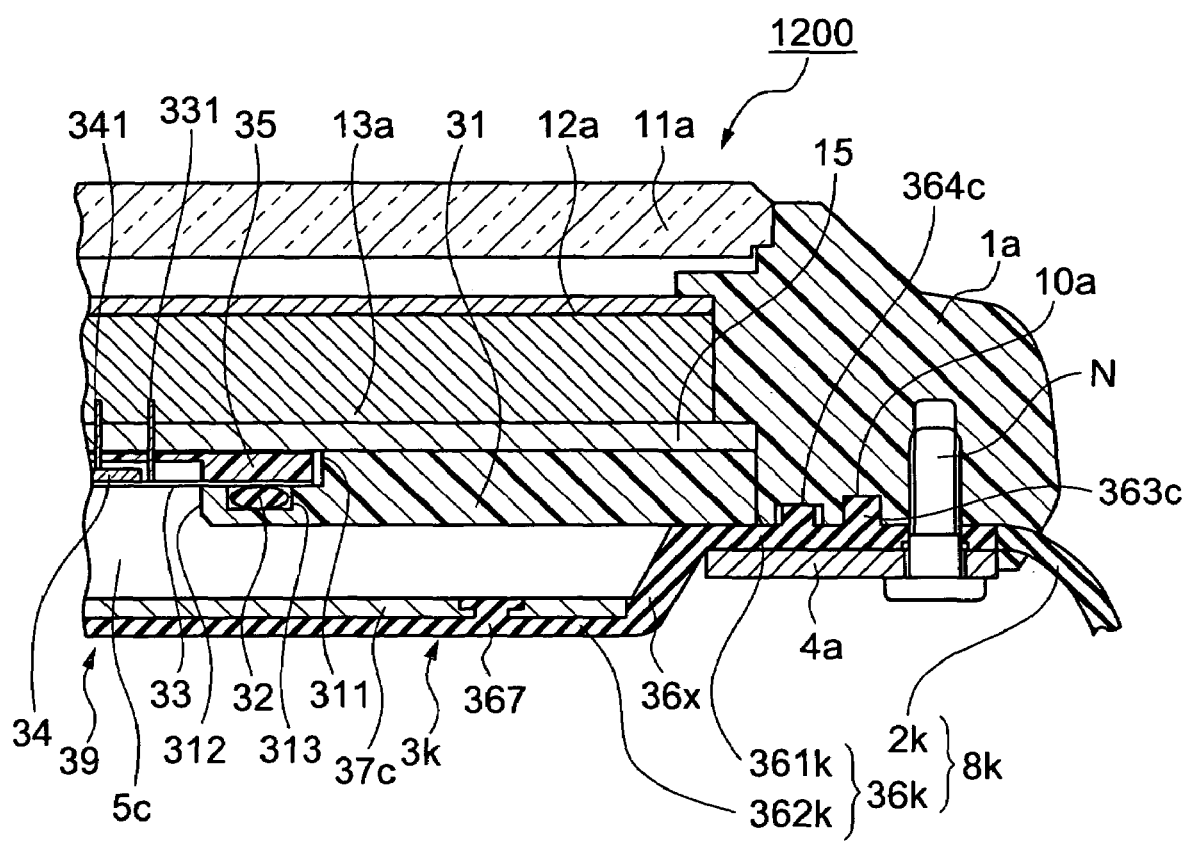
FIG. 19 is a fragmentary cross-sectional view of the embodiment 12 of the wristwatch.

As shown in FIGS. 18 and 19, a soft member 8k includes a band 2k being used to wear the body of the wristwatch on the user's wrist W, and an elastically deformable member 36k molded integral with the band 2k and forming the bottom of fluid chamber 5c that will come into contact with the user's wrist W. The deformable member 36k is elastically deformed depending on the pulsation transmitted from the band 2k. The soft member 8k is molded from a soft material, for example, of a higher vibration transmittance than the case 1a such as urethane or silicon for transmitting pulsation there through.

As shown in FIG. 19, a partition plate 15 that partitions the space within case 1a is provided on a lower surface of the timepiece function unit 13a. The plate 15 is molded, for example, from stainless steel (SUS) below which the pulsation measuring unit 3k is provided.

The bottom 39 of the fluid chamber 5c that will come into contact with the user's wrist is made of the elastically deformable member 36k that is elastically deformed depending on blood pulsation transmitted through the band 2k from the blood tubes of the user's wrist to thereby change the inner pressure within the fluid chamber 5c, and a deformation preventing member 37c bonded by vulcanization in a superposed manner to the inside of the deformable member 36k for deformation preventing purposes.

The deformable member 36k is provided at a position where it comes into contact with the user's wrist on which the body of the wristwatch 400 is worn. It is molded from a soft material elastically deformable depending on the pulsation from the blood tubes of the user's wrist. The soft material preferably includes, for example, urethane or silicon. The deformable member 36k has a fixing brim 361k which is fixed by a stop ring 4a to the case 1a and a downward protruding lower part 362k whose bottom will come into contact with the user's wrist. The fixing brim 361k has a ring-like ridge 363c provided on the case side and engaged in a recess 10a on the lower end of the case 1a such that the deformable member 36k does not deviate from its proper position.

The deformation preventing member 37c is bonded by vulcanization to the inside of the lower part 362k of the deformable member 36k.

The deformation preventing member 37c is molded from a hard material such as stainless steel. It prevents elastic deformation of the lower part 362k and causes the pressure of pulsation transmitted from the user's wrist to act evenly on the lower part 362k. The deformation preventing member 37c is molded integral with the lower part 362k with ridges 367 formed on the inner surface of the lower part 362k engaged in corresponding holes in the lower part of the deformation preventing member 36k.

The fixing brim 361k has a first ring-like ridge 364c inside the ridge 363c provided thereon and engaged in a recess 10a provided on a lower end of the case 1a. A second ridge 365k concentric with the first ridge 364c is formed on the opposite side of the fixing brim 361k from the first ridge 364c to abut on the stop ring 4a. The fixing brim 361k also has a third concentric ridge k provided inside the first ridge 364c on the case side and abutting the housing 31.

The lower part 362c protrudes downward from the housing 31 to thereby form the fluid chamber 5c there between.

While the soft member 8k is illustrated as molded from single plastic in this embodiment, it may be made of a plurality of plastic materials different in color or kind in so-called coinjection molding. For example, the deformable member 36c and the band 2k may be made of different plastic materials, respectively. For example, the band 2k and the deformable member 36k may be colored in blue and yellow or in other different colors, respectively.

The wristwatch 1200 of the embodiment 12 produces advantageous effects similar to those produced by the embodiment 4. In addition, the deformable member 36k and the band 2k are molded as a unit by the soft material. Blood pulsation in the blood tubes of the user's wrist is transmitted sequentially to the band 2k and the bottom or wall 39 integral with the band. Thus, the pulsation is transmitted rapidly and securely to the wall 39. Thus, the pulsation can be measured with high accuracy based on changes in the air pressure within the fluid chamber 5c. In addition, the number of parts and man-hours of the wristwatches, and their cost are reduced compared to the prior-art wristwatches in which the band 2k and the deformable member 36k are made of corresponding different materials.

Since the soft member 8k has a high vibration transmittance compared to the case 1a, it can transmit the pulsation to the pulsation measuring unit 3k more efficiently.

When the soft member 8k is molded from a plurality of different soft members as a unit, it can provide various designs even when they have the same shape.

When the deformable member 36k and the band 2k are made of a soft material of a high pulsation transmittance where the pulsation is transmitted from the band 2k to the deformable member 36k, the pulsation is efficiently transmitted to the fluid chamber 5c.

Embodiment 13

An embodiment 13 of the wristwatch according to the present invention will be described with reference to FIG. 20. The embodiment 13 has the same structure as the embodiment 5 except that the deformable member 36m and the band 2m are integrally molded from different materials. The points where the embodiment 13 is different from the embodiment 5 will be mainly described and further description of the embodiment 13 will be omitted.

Figure 20:
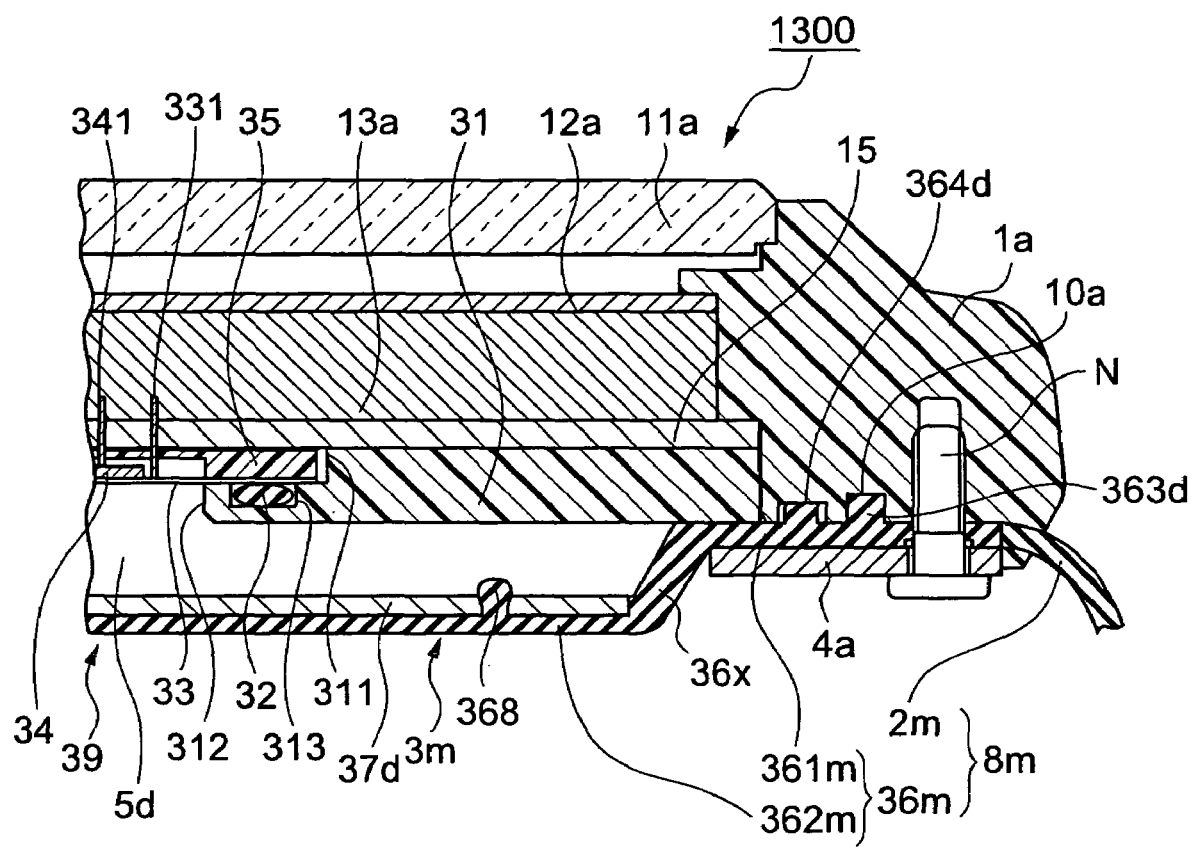
FIG. 20 is a fragmentary cross-sectional view of an embodiment 13 of the wristwatch.

As shown in FIG. 20, the wristwatch 1300 comprises a soft member 8m composed of a band 2m being used to wear the body of the wristwatch on the user's wrist, and an elastically deformable member 36m molded integral with the band 2m. The deformable member 36m forms the bottom of the fluid chamber 5d and is elastically deformable depending on the blood pulsation transmitted from the band 2m. The band 2m is molded from a soft material of a high pulsation transmittance that transmits the pulsation therethrough to the deformable member 36m, for example, compared to the material of the case 1a. The material of the band 2m is preferably NBR. The deformable member 36m is molded from a soft material of a high pulsation transmittance through which the pulsation received from the band 2m passes, for example, compared to the material of the case 1a. The material of the deformable member 36m is preferably EPDM.

While in this embodiment the soft member 8m is illustrated as molded from a single kind of plastic, it may be made of a plurality of materials different in color or kind, in the so-called coinjection molding. For example, the deformable member 36m and the band 2m may be made of different plastic materials, respectively. The band 2m and the deformable member 36m may be colored in blue and yellow or in other different colors, respectively.

The wristwatch 1300 of the embodiment 13 produces advantageous effects similar to those produced by the embodiments 5 and 12. In addition, since the deformable member 36m and the band 2m are molded as a unit from EPDM and NBR, respectively. Thus, they come to have characteristics suitable therefor to thereby transmit the pulsation in the user's wrist to the fluid chamber 5d with high accuracy.

Embodiment 14

An embodiment 14 of the wristwatch according to the present invention will be described with reference to FIG. 21. The embodiment 14 has the same structure as the embodiment 6 excluding that the deformable member 36m is molded integral with the band 2m. Thus, the points where the embodiment 14 is different from the embodiment 6 will be mainly described and further description of the embodiment 14 will be omitted.

Figure 21:
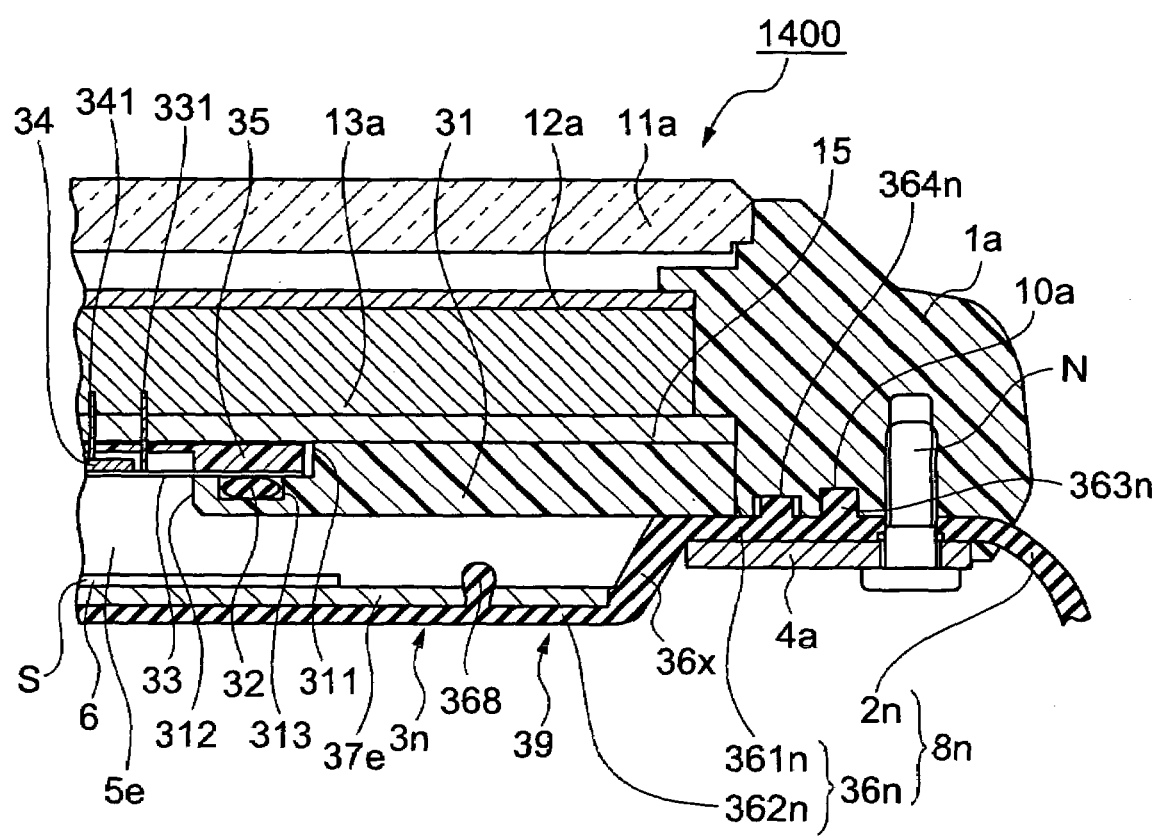
FIG. 21 is a fragmentary cross-sectional view of an embodiment 14 of the wristwatch.

As shown in FIG. 21, the wristwatch 1400 comprises a soft member 8n that in turn comprises the band 2n used to wear the body of the wristwatch on the user's wrist, and an elastically deformable member 36n molded integral with the band 2n and composing the bottom of the fluid chamber 5e that will come into contact with the user's wrist. The deformable member 36n is elastically deformed depending on blood pulsation transmitted from the band 2n. The band 2n and the deformable member 36n are molded integrally from a high pulsation transmittance material, for example, compared to the material of case 1a to transmit the pulsation therethrough. The material of the soft member 8n is preferably urethane or silicon.

The soft member 8n is molded colored in two or more colors. For example, the band 2n and the deformable member 36n may be colored in blue and yellow, respectively, or in more colors.

The wristwatch 1400 of the embodiment 14 produces advantageous effects similar to those produced by the embodiments 6 and 12.

Embodiment 15

An embodiment 15 of the wristwatch according to the present invention will be described with reference to FIG. 22. The embodiment 15 has the same structure as the embodiment 7 excluding that the deformable member 36p is molded integral with the band 2p. Thus, the points where the embodiment 15 is different from the embodiment 7 will be mainly described and further description of the embodiment 15 will be omitted.

Figure 22:
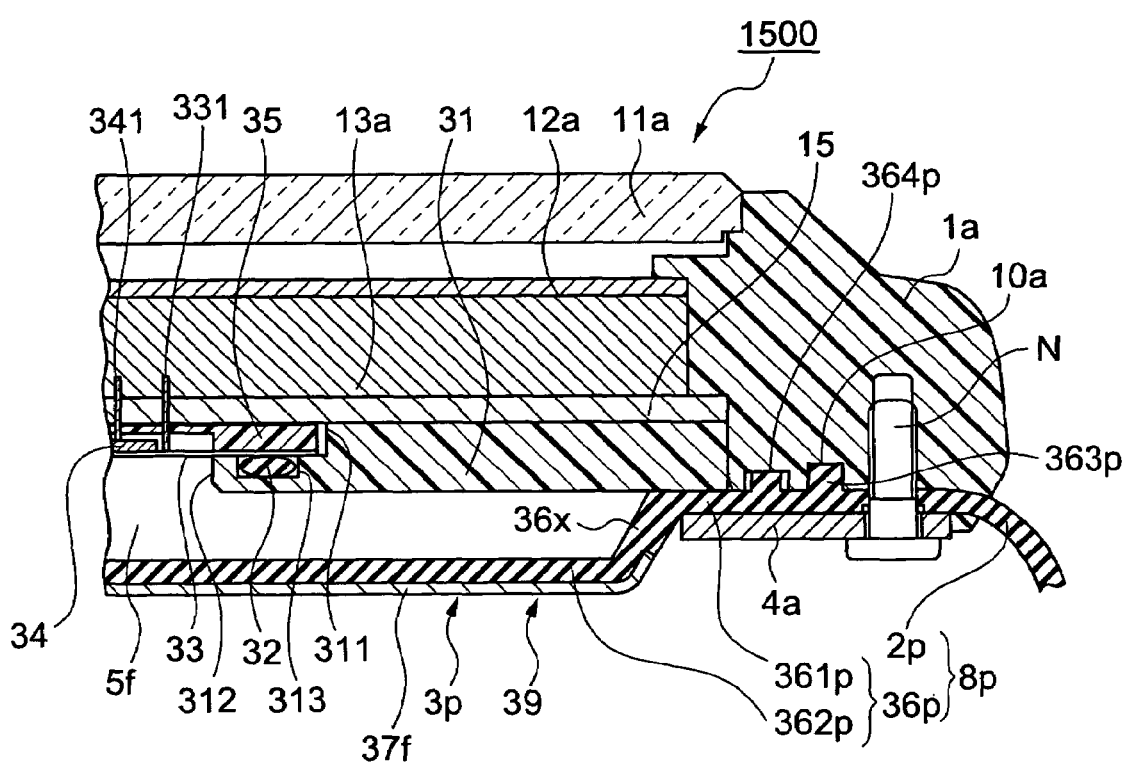
FIG. 22 is a fragmentary cross-sectional view of an embodiment 15 of the wristwatch.

As shown in FIG. 22, the wristwatch 1500 comprises a soft member 8p that in turn comprises the band 2p being used to wear the body of the wristwatch on the user's wrist, and the elastically deformable member 36p molded integral with the band 2p. The deformable member 36p composes the outer wall of the fluid chamber 5f including the bottom of the fluid chamber 5f. The deformable member 36p is elastically deformed depending on the pulsation transmitted from the band 2p. The band 2p and the deformable member 36p are molded from a high pulsation transmittance material, for example, compared to the material of case 1a to thereby transmit pulsation therethrough. The material of the soft member 8p is preferably urethane or silicon.

While in the embodiment the soft member 8p is molded from a single kind of plastic, it may be formed of plastic materials different in color or kind in the so-called coinjection molding. For example, the deformable member 36p and the band 2p may be formed out of plastic materials different in kind. Alternatively, for example, the band 2p and the deformable member 36p may be colored in blue and yellow, respectively, or in other different colors.

The embodiment 15 of the wristwatch 1500 produces advantageous effects similar to those produced by the embodiments 7 and 12.

Embodiment 16

An embodiment 16 of the wristwatch according to the present invention will be described with reference to FIG. 23. The embodiment 16 has the same structure as the embodiment 8 excluding that the deformable member 36r is molded integral with the band 2r. Thus, the points where the embodiment 16 is different from the embodiment 8 will be mainly described and further description of the embodiment 16 will be omitted.

Figure 23:
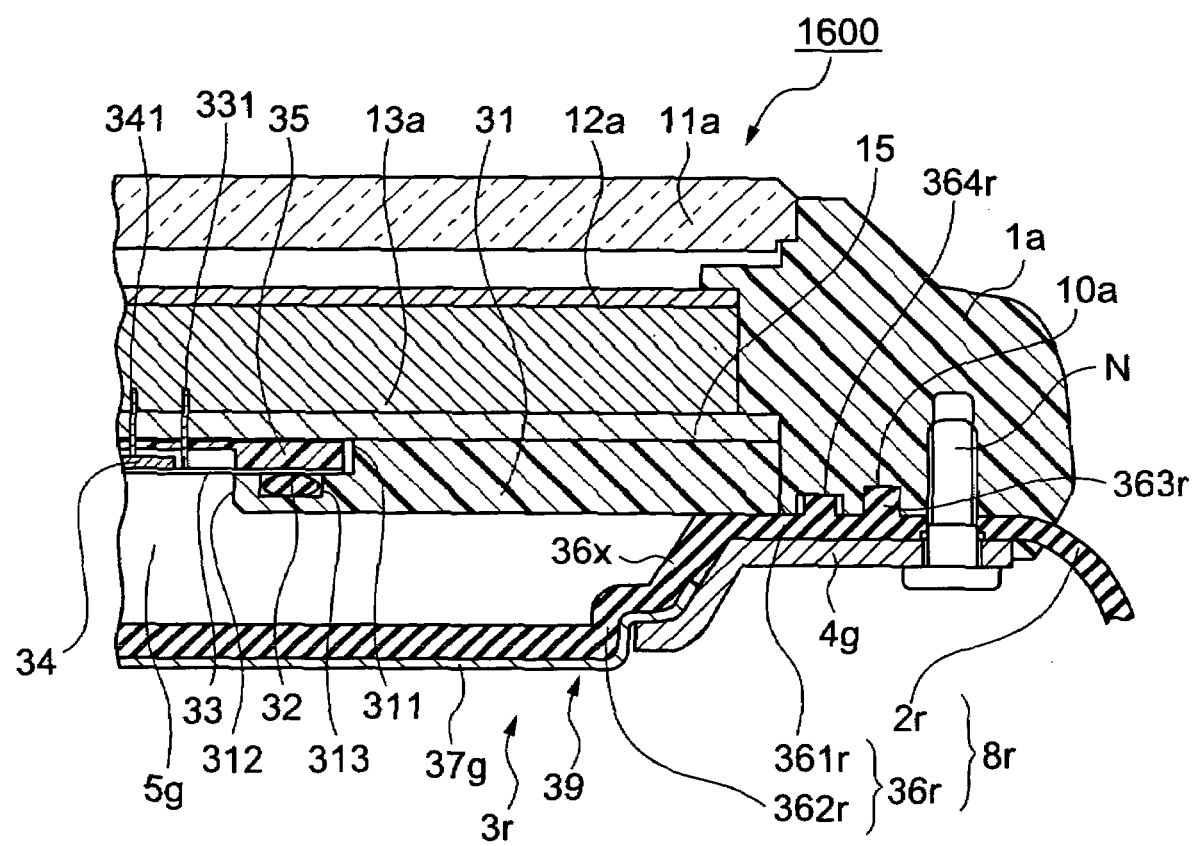
FIG. 23 is a fragmentary cross-sectional view of an embodiment 16 of the wristwatch.

As shown in FIG. 23, the wristwatch 1600 comprises the soft member 8r that in turn comprises a band 2r being used to wear the body of the wristwatch on the user's wrist, and the elastically deformable member 36r molded integral with the band 2r. The deformable member 36r composes the outer wall of the fluid chamber 5g whose bottom will come into contact with the user's wrist. The deformable member 36r is elastically deformed depending the pulsation transmitted from the band 2r. The band 2r and the deformable member 36r are molded from a high pulsation transmittance material, for example, compared to the material of case 1a to transmit pulsation therethrough. The material of the soft member 8r is preferably urethane or silicon.

While in the embodiment the soft member 8r is molded from a single kind of plastic, it may be formed of plastic materials different in color or kind in so-called coinjection molding. For example, the deformable member 36r and the band 2r may be formed out of plastic materials different in kind. Alternatively, for example, the band 2r and the deformable member 36r may be colored in blue and yellow, respectively, or in other different colors.

The embodiment 16 of the wristwatch 1600 produces advantageous effects similar to those produced by the embodiments 8 and 12.

Embodiment 17

An embodiment 17 of the wristwatch according to the present invention will be described with reference to FIG. 24. The embodiment 17 has the same structure as the embodiment 9 excluding that the deformable member 36s is molded integral with the band 2s. Thus, the points where the embodiment 17 is different from the embodiment 9 will be mainly described and further description of the embodiment 17 will be omitted.

Figure 24:
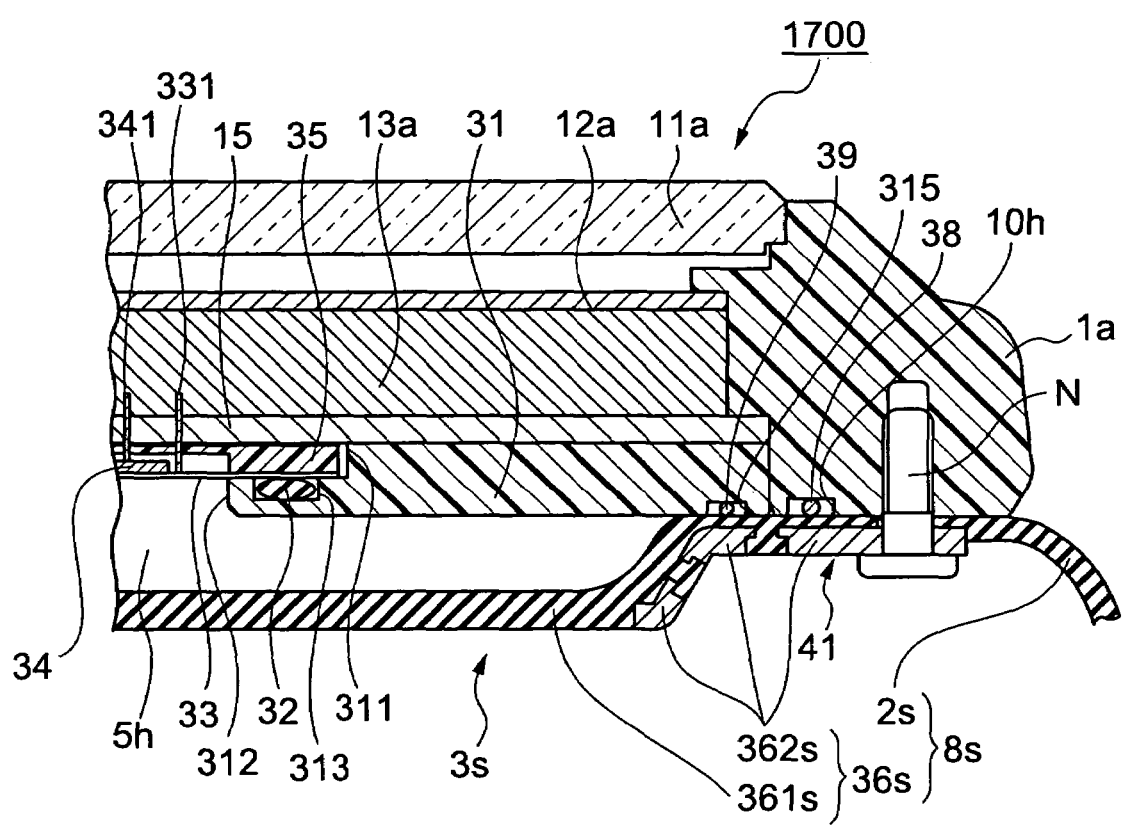
FIG. 24 is a fragmentary cross-sectional view of an embodiment 17 of the wristwatch.

As shown in FIG. 24, the wristwatch 1700 comprises a soft member 8s that in turn comprises the band 2s used to wear the body of the wristwatch on the user's wrist, and the elastically deformable member 36s molded integral with the band 2s. The deformable member 36s composes the outer wall of the fluid chamber 5h whose bottom that will come into contact with the user's wrist. The deformable member 36s is elastically deformed depending on the pulsation transmitted from the band 2s. The band 2s and the deformable member 36s are molded from a high pulsation transmittance material, for example, compared to the material of case 1a to transmit the pulsation therethrough. The material of the soft member 8s is preferably urethane or silicon.

While in the embodiment the soft member 8s is molded from a single kind of plastic, it may be formed of plastic materials different in color or kind in the coinjection molding. For example, the deformable member 36s and the band 2s may be formed out of plastic materials different in kind. Alternatively, for example, the band 2s and the deformable member 36s may be colored in blue and yellow, respectively, or in other different colors.

The embodiment 17 of the wristwatch 1700 produces advantageous effects similar to those produced by the embodiments 9 and 12.

Embodiment 18

An embodiment 18 of the wristwatch according to the present invention will be described with reference to FIG. 25. The embodiment 18 has the same structure as the embodiment 10 excluding that the deformable member 36t is molded integral with the band 2t. Thus, the points where the embodiment 18 is different from the embodiment 10 will be mainly described and further description of the embodiment 18 will be omitted.

Figure 25:
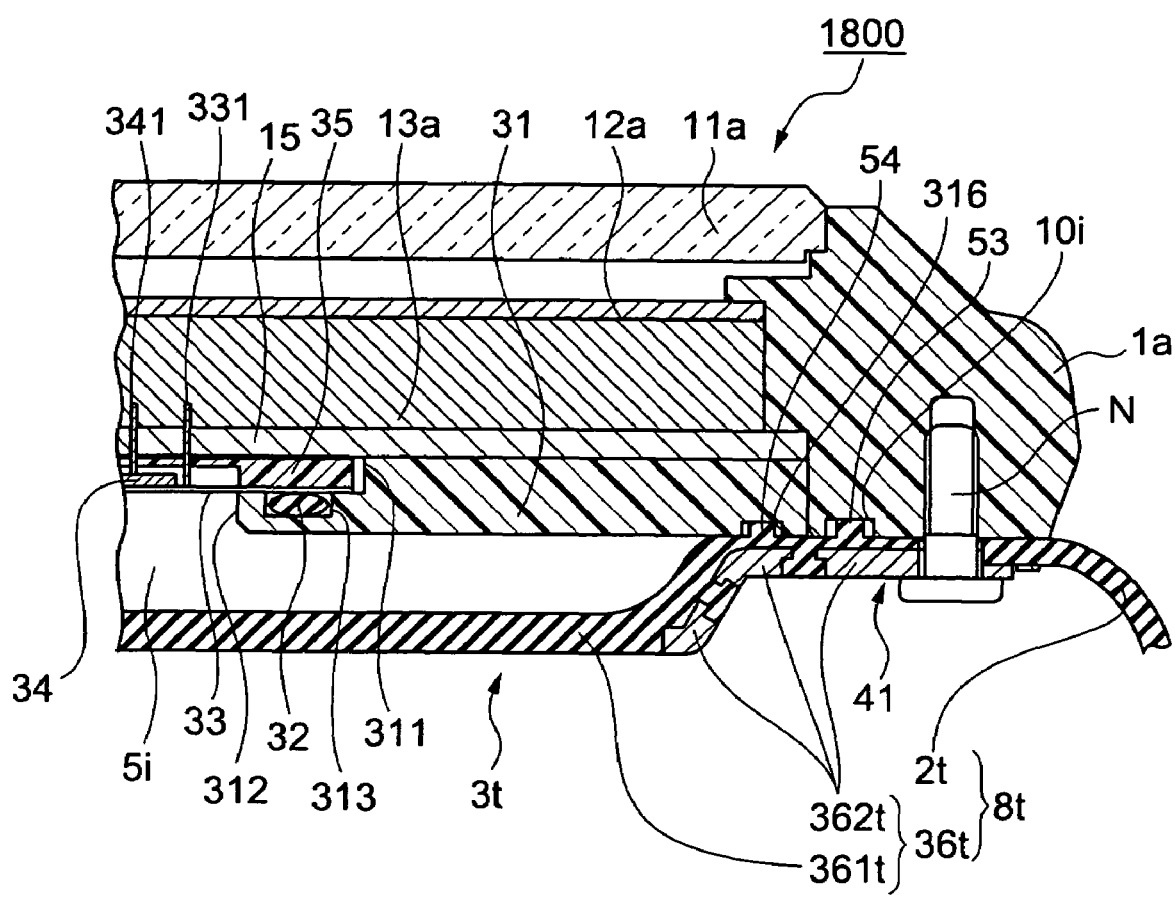
FIG. 25 is a fragmentary cross-sectional view of an embodiment 18 of the wristwatch.

As shown in FIG. 25, the wristwatch 1800 comprises a soft member 8t that in turn comprises the band 2t being used to wear the body of the wristwatch on the user's wrist, and the elastically deformable member 36t molded integral with the band 2t. The deformable member 36t composes the outer wall of the fluid chamber 5i whose wall will come into contact with the user's wrist. The deformable member 36t is elastically deformed depending on pulsation transmitted from the band 2t. The band 2t and the deformable member 36t are molded from a high pulsation transmittance material, for example, compared to the material of case 1a to transmit pulsation therethrough. The material of the soft member 8t is preferably urethane or silicon.

While in the embodiment the soft member 8t is molded from a single kind of plastic, it may be formed of plastic materials different in color or kind in the coinjection molding. For example, the deformable member 36t and the band 2t may be formed out of plastic materials different in kind. Alternatively, for example, the band 2t and the deformable member 36t may be colored in blue and yellow, respectively, or in other different colors.

The embodiment 18 of the wristwatch 1800 produces advantageous effects similar to those produced by the embodiments 10 and 12.

The present invention is not limited to the above embodiments. For example, the peripheral and first ridges are reversed in position. The number of ridges is not limited to three, but changeable depending on design. The announciator may produce a message in addition to an alarm sound.

While in the embodiment the wristwatch was illustrated as an example, the present invention is not limited to the wristwatches. For example, the present invention is applicable to wrist-worn devices that have no timepiece function.

The wristwatch may be worn on the user's upper arm or ankle excluding on the user's wrist.

CONCLUSION

As described above, in these embodiments the present invention provides a wrist-worn apparatus (100 in FIGS. 1 and 2; 400 in FIG. 9; 500 in FIG. 10; 600 in FIG. 11; 700 in FIG. 12; 800 in FIG. 13; 1200 in FIGS. 18 and 19; 1300 in FIG. 20; 1400 in FIG. 21; 1500 in FIG. 22; 1600 in FIG. 23) comprising:

a body of the apparatus; and a band (2 in FIGS. 1 and 2; 2a in FIGS. 9-13; 2k in FIGS. 18 and 19; 2m in FIG. 20; 2n in FIG. 21; 2p in FIG. 22; 2r in FIG. 23; 2s in FIG. 24; 2t in FIG. 25) attached to the body of the apparatus to be used for wearing the body of the apparatus on a user's wrist (W in FIG. 2);

the body of the apparatus comprising a pulsation sensing unit (3 in FIGS. 2 and 3; 3c in FIG. 9; 3d in FIG. 10; 3e in FIG. 11; 3f in FIG. 12; 3g in FIG. 13; 3k in FIGS. 18 and 19; 3m in FIG. 20; 3n in FIG. 21; 3p in FIG. 22; 3r in FIG. 23) that in turn comprises a pulsation sensing fluid chamber (5 in FIGS. 2 and 3; 5a in FIGS. 6 and 8; 5c in FIG. 9; 5d in FIG. 10; 5e in FIG. 11; 5f in FIG. 12; 5g in FIG. 13; 5h in FIG. 14; 5i in FIG. 15; 5j in FIG. 16) containing a fluid and having a bottom (362 in FIGS. 3 and 5; 362c in FIG. 9; 362d in FIG. 10; 362e in FIG. 11; 362f in FIG. 12; 362g in FIG. 13; 362k in FIGS. 18 and 19; 362m in FIG. 20; 362n in FIG. 21; 362p in FIG. 22; 362r in FIG. 23) that will come into contact with the user's wrist when the body of the apparatus is worn on the user's wrist, the fluid chamber having an outer wall (39 in FIGS. 3, 9-13, 18-23) defining the fluid chamber and comprising the bottom, the outer wall comprising an elastically deformable member (36 in FIGS. 2, 3 and 5; 36*c* in FIG. 9; 36*d* in FIG. 10; 36*e* in FIG. 11; 36*f* in FIG. 12; 36*g* in FIG. 13; 36*k* in FIGS. 18 and 19; 36*m* in FIG. 20; 36*n* in FIG. 21; 36*p* in FIG. 22; 36*r* in FIG. 23) elastically deformed depending on pulsation of blood in the blood tubes of the user's wrist transmitted through the band from the user's wrist when the body of the apparatus is worn on the user's wrist to thereby change the fluid pressure within the fluid chamber; and a deformation preventing member (37 in FIGS. 2 and 3; 37*c* in FIG. 9; 37*d* in FIG. 10; 37*e* in FIG. 11; 37*f* in FIG. 12; 37*g* in FIG. 13; 37*c* in FIGS. 18 and 19; 37*d* in FIG. 20; 37*e* in FIG. 21; 37*f* in FIG. 22; 37*g* in FIG. 23) provided on the bottom of the fluid chamber for preventing its elastic deformation.

According to this embodiment, since the deformable member that constitutes the outer wall of the pulsation sensing fluid chamber is elastically deformed depending on the pulsation of blood in the blood tubes of the user's wrist, changes occur in the fluid pressure within the fluid chamber. The deformation preventing member provided on the bottom of the fluid chamber made of the deformable member prevents the bottom of the fluid chamber from being deformed. Thus, changes in the fluid pressure within the fluid chamber are always made even. As a result, undesirable resulting vibration noise is reduced, thereby achieving pulsation measurement with high accuracy.

In one embodiment, the present invention provides a wrist-worn apparatus (1200 in FIGS. 18 and 19; 1300 in FIG. 20; 1400 in FIG. 21; 1500 in FIG. 22; 1600 in FIG. 23; 1700 in FIG. 24; 1800 in FIG. 25) comprising:

a body of the apparatus; and a band (2*k* in FIGS. 18 and 19; 2*m* in FIG. 20; 2*n* in FIG. 21; 2*p* in FIG. 22; 2*r* in FIG. 123; 2*s* in FIG. 24; 2*t* in FIG. 25) attached to the body of the apparatus to be used for wearing the body of the apparatus on a user's wrist (W in FIG. 18);

the body of the apparatus comprising a pulsation sensing unit (3*k* in FIGS. 18 and 19; 3*m* in FIG. 20; 3*n* in FIG. 21; 3*p* in FIG. 22; 3*r* in FIG. 23; 3*s* in FIG. 24; 3*t* in FIG. 25) that in turn comprises a pulsation sensing fluid chamber (5*c* in FIGS. 18 and 19; 5*d* in FIG. 20; 5*e* in FIG. 21; 5*f* in FIG. 22; 5*g* in FIG. 23; 5*h* in FIG. 24; 5*i* in FIG. 25) containing a fluid and having a bottom will come into contact with the user's wrist when the body of the apparatus is worn on the user's wrist, the fluid chamber having an outer wall (39 in FIGS. 2, 3, 9-13 and 18-23) that defines the fluid chamber, the outer wall and the band being molded integral with each othre and made of a soft material (8*k* in FIGS. 18 and 19; 8*m* in FIG. 20; 8*n* in FIG. 21; 8*p* in FIG. 22; 8*r* in FIG. 23; 8*s* in FIG. 25; 8*t* in FIG. 26).

According to this embodiment, since the outer wall that defines the fluid chamber and the band are molded integral with each other and made of the soft material, pulsation of blood in the blood tubes of the user's wrist is transmitted to the band and the outer wall sequentially and hence securely and rapidly to thereby allow pulsation measurement with high accuracy. This embodiment reduces the number of parts, man-hours for assembly and cost of the apparatus compared to the prior art device in which the band and the outer wall that constitutes the fluid chamber are made of different materials.

In one embodiment, the present invention provides a wrist-worn apparatus (100 in FIGS. 1 and 2; 200 in FIG. 6; 300 in FIG. 8; 400 in FIG. 9; 500 in FIG. 10; 600 in FIG. 11; 700 in FIG. 12; 800 in FIG. 13; 900 in FIG. 14; 1000 in FIG. 15; 1100 in FIG. 16; 1200 in FIGS. 18 and 19; 1300 in FIG. 20; 1400 in FIG. 21; 1500 in FIG. 22; 1600 in FIG. 23; 1700 in FIG. 24; 1800 in FIG. 25) comprising:

a body of the apparatus; and a band (2 in FIGS. 1 and 2; 2*a* in FIGS. 6, 8-16; 2*k* in FIGS. 18 and 19; 2*m* in FIG. 20; 2*n* in FIG. 21; 2*p* in FIG. 22; 2*r* in FIG. 23; 2*s* in FIG. 24; 2*t* in FIG. 25) attached to the body of the apparatus to be used for wearing the body of the apparatus on the user's wrist (W in FIGS. 2 and 18); and the body of the apparatus comprising a pulsation measuring unit (3 in FIGS. 2 and 3; 3*a* in FIG. 6; 3*b* in FIG. 8; 3*c* in FIG. 9; 3*d* in FIG. 10; 3*e* in FIG. 11; 3*f* in FIG. 12; 3*g* in FIG. 13; 3*h* in FIG. 14; 3*i* in FIG. 15; 3*j* in FIG. 16; 3*k* in FIGS. 18 and 19; 3*m* in FIG. 20; 3*n* in FIG. 21; 3*p* in FIG. 22; 3*r* in FIG. 23; 3*s* in FIG. 24; 3*t* in FIG. 25) that in turn comprises a pulsation sensing fluid chamber (5 in FIGS. 2 and 3; 5*a* in FIGS. 6 and 8; 5*c* in FIGS. 9, 18 and 19; 5*d* in FIGS. 10 and 20; 5*e* in FIGS. 11 and 21; 5*f* in FIGS. 12 and 22; 5*g* in FIGS. 13 and 23; 5*h* in FIGS. 14 and 24; 5*i* in FIGS. 15 and 25; 5*j* in FIG. 16) that contains a fluid and that will come into contact with the user's wrist when the body of the apparatus is worn on the user's wrist, and a pulsation sensor (34 in FIGS. 2-25) provided within the pulsation sensing fluid chamber for sensing changes in the fluid pressure within the fluid chamber as pulsation of blood in the blood tubes of the user's wrist, the sensor being positioned at a position (340) deviating from the center (50) of the fluid chamber.

According to this embodiment, the sensor that senses changes in the fluid pressure within the fluid chamber and outputs the sensed pressure change to the pulsation measuring unit deviates from the center of the fluid chamber. Thus, the sensor does not directly get at its center the changes in the fluid pressure within the fluid chamber based on the pulsation of blood in the blood tubes of the user's wrist transmitted from the user's wrist through the band. Thus, a direct influence of changes in the pressure within the fluid chamber on the sensor is prevented, thereby allowing the changes in the pressure within the fluid chamber to be sensed indirectly and hence pulsation measurement is made with high accuracy.

In one embodiment, the present invention provides a wrist-worn apparatus (100 in FIGS. 1 and 2; 200 in FIG. 6; 300 in FIG. 8; 400 in FIG. 9; 500 in FIG. 10; 600 in FIG. 11; 700 in FIG. 12; 800 in FIG. 13; 900 in FIG. 14; 1000 in FIG. 15; 1100 in FIG. 16; 1200 in FIGS. 18 and 19; 1300 in FIG. 20; 1400 in FIG. 21; 1500 in FIG. 22; 1600 in FIG. 23; 1700 in FIG. 24; 1800 in FIG. 25) comprising:

a body of the apparatus; and a band (2 in FIGS. 1 and 2; 2*a* in FIGS. 6, 8-16; 2*k* in FIGS. 18 and 19; 2*m* in FIG. 20; 2*n* in FIG. 21; 2*p* in FIG. 22; 2*r* in FIG. 23; 2*s* in FIG. 24; 2*t* in FIG. 25) attached to the body of the apparatus to be used for wearing the body of the apparatus on a user's wrist (W in FIGS. 2 and 18);

the body of the apparatus comprising a pulsation sensing unit (3 in FIGS. 2 and 3; 3*a* in FIG. 6; 3*b* in FIG. 8; 3*c* in FIG. 9; 3*d* in FIG. 10; 3*e* in FIG. 11; 3*f* in FIG. 12; 3*g* in FIG. 13; 3*h* in FIG. 14; 3*i* in FIG. 15; 3*j* in FIG. 16; 3*k* in FIGS. 18 and 19; 3*m* in FIG. 20; 3*n* in FIG. 21; 3*p* in FIG. 22; 3*r* in FIG. 23; 3*s* in FIG. 24; 3*t* in FIG. 25;) that in turn comprises a pulsation sensing fluid chamber (5 in FIGS. 2 and 3; 5*a* in FIGS. 6 and 8; 5*c* in FIGS. 9, 18 and 19; 5*d* in FIGS. 10 and 20; 5*e* in FIGS. 11 and 21; 5*f* in FIGS. 12 and 22; 5*g* in FIGS. 13 and 23; 5*h* in FIGS. 14 and 24; 5*i* in FIGS. 15 and 25; 5*j* in FIG. 16) containing a fluid and having a bottom that will come into contact with the user's wrist when the body of the apparatus is worn on the user's wrist, the fluid chamber having an outer wall (39 in FIGS. 2, 3, 9-13, 18-23) that defines the fluid chamber and that comprises the bottom, the outer wall comprising an elastically deformable member (36 in FIGS. 2, 3 and 5; 36a in FIGS. 6 and 7; 36b in FIG. 8; 36c in FIG. 9; 36d in FIG. 10; 36e in FIG. 11; 36f in FIG. 12; 36g in FIG. 13; 36h in FIG. 14; 36i in FIG. 15; 36j in FIGS. 16 and 17; 36k in FIGS. 18 and 19; 36m in FIG. 20; 36n in FIG. 21; 36p in FIG. 22; 36r in FIG. 23; 36s in FIG. 26; 36t in FIG. 25) elastically deformed depending on pulsation of blood in the blood tubes of the user's wrist transmitted through the band from the user's wrist when the body of the apparatus is worn on the user's wrist to thereby change the fluid pressure within the fluid chamber; and a deformation preventing member (37 in FIGS. 2 and 3; 37c in FIG. 9; 37d in FIG. 10; 37e in FIG. 11; 37f in FIG. 12; 37g in FIG. 13) bonded by vulcanization to the bottom of the fluid chamber for preventing its elastic deformation.

According to this embodiment, since the deformable member that defines the outer wall of the fluid chamber is elastically deformed depending on pulsation of blood in the blood tubes of the user's wrist, the fluid pressure within the fluid chamber changes to thereby allow pulsation measurement with high accuracy. The deformation preventing member provided on the bottom of the fluid chamber made of the deformable member prevents the the bottom of the fluid chamber from being elastically deformed. Thus, changes in the pressure within the fluid chamber are always made even. As a result, undesirable vibration noise is reduced to thereby achieve pulsation measurement with high accuracy.

When the pulsation is transmitted from the user's wrist to the bottom of the fluid chamber made of the deformable member and the deformation preventing member before being transmitted to the fluid chamber, the bottom of the fluid chamber tries to be elastically deformed depending on the pulsation while the deformation preventing member tries to prevent the bottom of the fluid chamber from being elastically deformed. Thus, they try to detach away from each other. However, they are bonded integrally by vulcanization. Thus, it is ensured to prevent them from being detached away from each other.

In one embodiment, the body of the apparatus further comprises a case (1 in FIGS. 1 and 2; 1a in FIGS. 6, 8-16) for the body of the apparatus; the deformable member having a brim (361 in FIGS. 3 and 5; 361a in FIGS. 6 and 7; 361b in FIG. 8; 361c in FIG. 9; 361d in FIG. 10; 361e in FIG. 11; 361f in FIG. 12; 361g in FIG. 13; 361j in FIG. 16), the body of the apparatus further comprisinfluidtop member (4 in FIG. 3; 4a in FIGS. 9-12; 4g in FIG. 13; 4a in FIGS. 19-23) that fixes the deformable member at its brim to the case in a pressed state, the brim comprising a first ring-like ridge (363 in FIGS. 3 and 5; 363a in FIGS. 6, 7; 363b in FIG. 8; 363c in FIG. 9; 363d in FIG. 10; 363e in FIG. 11; 363f in FIG. 12; 363g in FIG. 13) abutting on the case and a second ring-like ridge (364 in FIGS. 3 and 5; 364a in FIGS. 6 and 7; 364b in FIG. 8; 364c in FIG. 9; 364d in FIG. 10; 364e in FIG. 11; 364f in FIG. 12; 364g in FIG. 13) abutting on the stop member.

According to this embodiment, since the stop member that fixes the deformable member at its brim to the case is further provided, airtightness of the inside of the case is ensured.

In one such embodiment, the body of the apparatus further comprises a case (1 in FIG. 2; 1a in FIGS. 6-13, 16) for the body of the apparatus and the deformable member that composes the bottom of the fluid chamber (362 in FIGS. 3 and 5; 362a in FIGS. 6 and 7; 362b in FIG. 8; 362c in FIG. 9; 362d in FIG. 10; 362e in FIG. 11; 362f in FIG. 12; 362g in FIG. 13; 362j in FIG. 16) is made of a material having a higher elasticity than the brim, the bottom of the fluid chamber being made of a material having resistance to the environment.

According to this embodiment, since the brim exhibits a small force repelling the pressing force given to the brim by the press member, the stop member maintains the brim in a pressed state, thereby improving airtightness of the case inside. The deformable member bottom of the fluid chamber exhibits resistance to changes in the environment to thereby improve the durability of the elastically deformable member.

In one such embodiment, the deformation preventing member is fixed to an inner surface of the bottom of the fluid chamber.

According to this embodiment, since the deformation preventing member is fixed to the inner surface of the bottom of the fluid chamber, it does not touch the user's wrist when the apparatus is worn. Thus, the strength and rigidity of the apparatus are improved while maintaining its fitness and pleasant texture to the user.

In one embodiment, the deformation preventing member is provided inside the bottom of the fluid chamber such that a space is formed between the deformation preventing member and the bottom of the fluid chamber, and further comprising an announciator (6 in FIG. 11) provided on the deformation preventing member in the space between the deformation preventing member and the bottom of the fluid chamber.

According to this embodiment, the deformation preventing member is spaced apart from the bottom of the fluid chamber inside the fluid chamber. Thus, the deformable member can transmit sound from the announciator to the outside without absorbing possible vibrations produced by the deformation preventing member.

In one embodiment, the deformation preventing member is fixed to an outer surface of the bottom of the fluid chamber.

According to this embodiment, since the deformation preventing member is fixed to the outer surface of the bottom of the fluid chamber, the deformable member neither directly gets an external shock nor comes into contact with an external object. In addition, no deformation preventing members are provided on the deformable member except on the bottom of the fluid chamber. Thus, the bottom of the fluid chamber itself is elastically deformable while preventing cracks from being formed in the deformable member provided inside the deformation preventing member.

In one such embodiment, the stop member is superimposed on the brim of the deformation preventing member.

According to this embodiment, the stop member is superimposed on the brim of the deformation preventing member. Thus, the bottom of the fluid chamber is completely covered by the deformation preventing member and the stop member. Thus, an external shock and an external object are directly gotten and touched, respectively, by the deformation preventing member and the stop member, thereby preventing the deformable member from being cracked. Since no deformation preventing members are provided on the deformable member except on the bottom of the fluid chamber although the deformable member is completely covered, the bottom of the fluid chamber itself is elastically deformable while preventing the deformable member provided inside the deformation preventing member from being cracked.

In one embodiment, the deformation preventing member and the bottom of the fluid chamber are molded integral with each other.

According to this embodiment, the deformation preventing member and the bottom of the fluid chamber are molded integral with each other. Thus, no work such as coating the deformation preventing member and the bottom of the fluid chamber with an adhesive by hand and then bonding both together by hand is needed. This leads to reducing man-hours of the apparatuses and improving its productivity.

In one embodiment, the stop member comprises a ridge (365j in FIGS. 16 and 17) provided thereon and engaged in a recess (365i in FIGS. 16 and 17) provided on the deformable member.

According to this embodiment, since the ridge of the stop member is engaged in the recess in the deformable member to thereby prevent the deformable member from deviating from its proper position and maintain airtightness of the inside of the case.

In one embodiment, the deformable member comprises a soft part (361h in FIG. 14; 361i in FIG. 15; 361s in FIG. 24; 361t in FIG. 25) made of a soft material elastically deformable depending on a force exerted from the user's wrist on which the body of the apparatus is worn, and a hard part (362h in FIG. 14; 362i in FIG. 15; 362s in FIG. 24; 362t in FIG. 25) made of a harder material than the soft material and including at least the brim thereof fixed to the case.

According to this embodiment, the deformable member is directly fixed to the case at a position of the hard part in a pressed state. Thus, the deformable member does not deviate from its proper position while maintaining airtightness of the inside of the case. In addition, the deformable member comprises the soft part made of a soft material elastically deformable depending on a force exerted from the user's wrist on which the body of the apparatus is worn. Thus, fitness and pleasant texture of the deformable member to the user's wrist is maintained well. Furthermore, no soft member (such as for example, a cuff) need be superimposed on the deformable member, thereby preventing an increase in the thickness of the apparatus. Since no member that presses the deformable member to the case is needed, the number of parts of the apparatus and their weight and size are reduced.

In one embodiment, the hard part is made of metal or plastic and molded integral with the soft part.

According to this embodiment, the hard part is made of metal or plastic, and the hard part is molded integral with the soft part.

In one embodiment, the body of the apparatus further comprises a case for the body of the apparatus, and the soft material has a higher vibration transmittance than the material of the case.

According to this embodiment, the soft material has a higher vibration transmittance than the material of the case. Thus, pulsation can be transmitted efficiently to the pulsation sensing fluid chamber.

In one embodiment, the soft material comprises a plurality of different soft members molded integral with each other.

According to this embodiment, the soft material comprises a plurality of different soft members molded integral with each other. Thus, the plurality of soft members of the same shape can have different designs to thereby improve designability.

In one embodiment, the deformable member and the band are made of a soft material of a high pulsation transmittance to transmit pulsation therethrough.

According to this embodiment, the deformable member and the band are made of a soft material of a high pulsation transmittance to transmit pulsation therethrough. Thus, pulsation can be transmitted more efficiently to the pulsation sensing fluid chamber.

In one embodiment, the sensor comprises a piezoelectric element (34 in FIGS. 2, 3, 6, 8-16, 18-25) that converts changes in the pressure within the fluid chamber to an electric signal.

According to this embodiment, the piezoelectric element is capable of converting changes in the pressure within the fluid chamber into an electric signal.

In one embodiment, the body of the apparatus further comprises a case (1 in FIG. 2; 1a in FIGS. 6, 8-16, 18-25) for the body of the apparatus, and the case has housed a timepiece function unit (13 in FIG. 2; 13a in FIGS. 6, 8-16, 18-25) that counts time, and a display (12 in FIGS. 1 and 2; 12a in FIGS. 6, 8-16, 18-25) that displays the counted time.

According to this embodiment, the case has housed the timepiece function unit and the display unit. Thus, it can be used as a device that displays time and senses pulsation.

Various modifications and changes may be made thereunto without departing from the broad spirit and scope of this invention. The above-described embodiments are intended to illustrate the present invention, not to limit the scope of the present invention. The scope of the present invention is shown by the attached claims rather than the embodiments. Various modifications made within the meaning of an equivalent of the claims of the invention and within the claims are to be regarded to be in the scope of the present invention.

This application is based on Japanese Patent Application No. 2003-154563 and No. 2003-170598 and each including specification, claims, drawings and summary. The disclosure of the above Japanese patent application is incorporated herein by reference in its entirety.

What is claimed is:

1. A wrist-worn apparatus comprising:
   a body of the apparatus; and
   a band attached to the body of the apparatus for wearing the body of the apparatus on a user's wrist;
   wherein the body of the apparatus comprises:
      a pulsation sensing unit that includes a pulsation sensing fluid chamber which contains a fluid and which comprises a bottom that comes into contact with the user's wrist when the body of the apparatus is worn on the user's wrist, the fluid chamber having an outer wall which includes the bottom of the fluid chamber and which defines the fluid chamber, the outer wall comprising an elastically deformable member which is elastically deformed depending on pulsation of blood in blood vessels of the user's wrist, said pulsation being transmitted through the band from the user's wrist when the body of the apparatus is worn on the user's wrist to thereby change a fluid pressure within the fluid chamber; and
      a deformation preventing member provided on the bottom of the fluid chamber for preventing elastic deformation of the fluid chamber;
   wherein the deformable member includes a brim, and the body of the apparatus further comprises a case and a stop member that fixes the deformable member in a pressed state at the brim to the case, and wherein the brim comprises a first ring-like ridge abutting on the case and a second ring-like ridge abutting on the stop member.

2. The wrist-worn apparatus of claim 1, wherein a portion of the deformable member that composes the bottom of the fluid chamber is made of a material having a higher elasticity than the brim, and the bottom of the fluid chamber is made of a material having resistance to the environment.

3. The wrist-worn apparatus of claim 2, wherein the deformation preventing member is fixed to an inner surface of the bottom of the fluid chamber.

4. The wrist-worn apparatus of claim 3, wherein the deformation preventing member and the bottom of the fluid chamber are molded integrally with each other.

5. The wrist-worn apparatus of claim 2, wherein the deformation preventing member is provided inside the bottom of the fluid chamber such that a space is formed between the deformation preventing member and the bottom of the fluid chamber, and the body of the apparatus further comprises an announciator provided on the deformation preventing member in the space between the deformation preventing member and the bottom of the fluid chamber.

6. The wrist-worn apparatus of claim 2, wherein the deformation preventing member is fixed to an outer surface of the bottom of the fluid chamber.

7. The wrist-worn apparatus of claim 6, wherein the stop member is superimposed on a brim of the deformation preventing member.

8. The wrist-worn apparatus of claim 2, wherein the stop member comprises a ridge provided thereon and engaged in a recess provided on the deformable member.

9. The wrist-worn apparatus of claim 2, wherein the deformable member comprises a soft part made of a soft material elastically deformable depending on a force exerted from the user's wrist on which the body of the apparatus is worn, and a hard part made of a harder material than the soft material and including at least the brim, which is fixed to the case.

10. The wrist-worn apparatus of claim 9, wherein the hard part comprises one of metal and plastic and is molded integrally with the soft part.

* * * * *